(12) United States Patent
Alleyne et al.

(10) Patent No.: US 10,084,143 B2
(45) Date of Patent: *Sep. 25, 2018

(54) PHOSPHORESCENT MATERIALS

(71) Applicant: Universal Display Corporation, Ewing, NJ (US)

(72) Inventors: Bert Alleyne, Ewing, NJ (US); Raymond Kwong, Plainsboro, NJ (US); Walter Yeager, Yardley, PA (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 524 days.

This patent is subject to a terminal disclaimer.

(21) Appl. No.: 14/691,835

(22) Filed: Apr. 21, 2015

(65) Prior Publication Data
US 2015/0255734 A1   Sep. 10, 2015

Related U.S. Application Data

(62) Division of application No. 12/559,764, filed on Sep. 15, 2009, now Pat. No. 9,034,483.
(Continued)

(51) Int. Cl.
*H01L 51/54* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |

(Continued)

FOREIGN PATENT DOCUMENTS

| | | |
|---|---|---|
| CN | 101006161 | 7/2007 |
| EP | 0650955 | 5/1995 |

(Continued)

OTHER PUBLICATIONS

EPO Communication and Extended European Search Report dated Feb. 19, 2016 for corresponding EP Application No. 5191449.6.
(Continued)

Primary Examiner — Marie R. Yamnitzky
(74) Attorney, Agent, or Firm — Duane Morris LLP

(57) ABSTRACT

A compound selected from

Compound 1

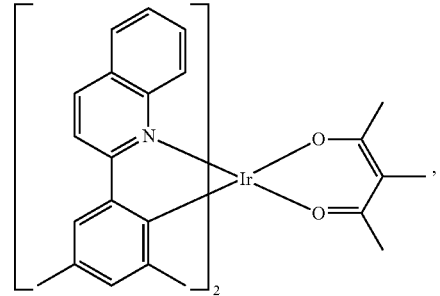

Compound 2

Compound 8

Compound 9

(Continued)

-continued

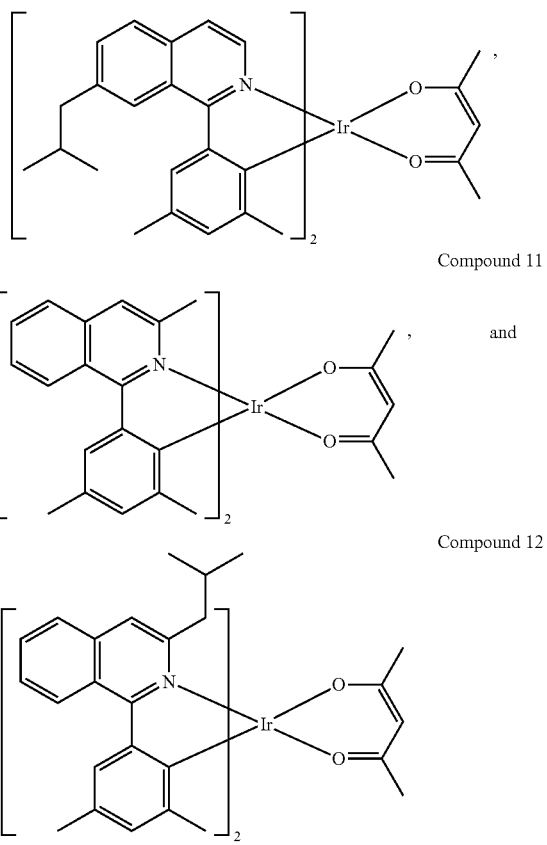

Compound 10

Compound 11

Compound 12 is provided. An organic light emitting device including an anode, cathode, and organic layer disposed between the anode and cathode, including one of the compounds is also provided.

14 Claims, 3 Drawing Sheets

Related U.S. Application Data

(60) Provisional application No. 61/097,488, filed on Sep. 16, 2008.

(51) Int. Cl.
H01L 51/00 (2006.01)
C07F 15/00 (2006.01)
H01L 51/50 (2006.01)
H01L 51/52 (2006.01)

(52) U.S. Cl.
CPC  C09K 2211/1029 (2013.01); C09K 2211/185 (2013.01); H01L 51/5016 (2013.01); H01L 51/5056 (2013.01); H01L 51/5072 (2013.01); H01L 51/5088 (2013.01); H01L 51/5206 (2013.01); H01L 51/5221 (2013.01); H01L 2251/301 (2013.01); H01L 2251/308 (2013.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,265,224 B2 | 9/2007 | Park et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,269,317 B2 | 9/2012 | Alleyne et al. |
| 8,431,243 B2 * | 4/2013 | Kwong et al. ...... C07F 15/0033 313/502 |
| 9,142,786 B2 * | 9/2015 | Kwong et al. ...... C07F 15/0033 |
| 9,577,201 B2 * | 2/2017 | Kwong et al. ...... C07F 15/0033 |
| 9,911,930 B2 * | 3/2018 | Kwong et al. ...... H01L 51/0085 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0068526 A1 | 4/2003 | Kamatani et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0004918 A1 | 1/2007 | Jeong et al. |
| 2007/0104980 A1 | 5/2007 | Kim et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |

(56) References Cited

U.S. PATENT DOCUMENTS

| | | |
|---|---|---|
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0078317 A1 | 3/2009 | Kim et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 1725079 | 11/2006 |
| EP | 2034538 | 3/2009 |
| JP | 200511610 | 1/2005 |
| JP | 2007123392 | 5/2007 |
| JP | 2007207916 | 8/2007 |
| JP | 2007254297 | 10/2007 |
| JP | 2008074939 | 4/2008 |
| KR | 100662430 | 12/2006 |
| WO | 2001039234 | 5/2001 |
| WO | 2002002714 | 1/2002 |
| WO | 200215645 | 2/2002 |
| WO | 02/44189 | 6/2002 |
| WO | 2003040257 | 5/2003 |
| WO | 2003060956 | 7/2003 |
| WO | 20041016711 | 2/2004 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 20050112520 | 11/2005 |
| WO | 2005123873 | 12/2005 |
| WO | 2006009024 | 1/2006 |
| WO | 20061000544 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 20061095943 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 20071143201 | 12/2007 |
| WO | 2008056746 | 5/2008 |
| WO | 2008101842 | 8/2008 |
| WO | 20080109824 | 9/2008 |
| WO | 20081109824 | 9/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010033550 | 3/2010 |

OTHER PUBLICATIONS

Office Action dated Sep. 29, 2012 in Chinese Application No. 200980140491.7.

Xu, Ling-ling et al., "Study on photoluminescent and electroluminescent characteristic of cyclometalated platinum complexes with long chain β-diketonate ancillary ligands", Journal of Functional Materials, 2007, vol. 38, No. 11, pp. 1766-1768 (English abstract provided).

Luo, Kai-jun et al., "Microwave Synthesis and Electroluminescent Characteristic of Phosphorescent Cyclometalated Platinum Complexes with Long Chain β-diketonate Ancillary Ligands", Journal of Sichuan University (Engineering Science Edition), 2007, vol. 39, No. 5, pp. 53-58 (English abstract provided).

Chen, Jun-Rong et al., "Theoretical Studies on Electronic Spectra and Second-order Nonlinear Optical Properties of Cyclometalated Platinum Complexes with Long Chain β-Diketonate Ancillary Ligands", ACTA Chimica Sinica, 2008, vol. 66, No. 13, pp. 1513-1517 (English abstract provided).

Luo, Kai-jun et al., "Rapid synthesis of phosphorescent cyclometalated platinum complexes by microwave irradiation", Chemical Research and Application, 2007, vol. 19, No. 9, pp. 991-993 (English abstract provided).

Notice of Reasons for Rejection dated Jul. 11, 2016 in corresponding JP Application No. 2015-137987.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3 (2007).

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1:15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

(56) References Cited

OTHER PUBLICATIONS

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1)162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of @-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based On Silole Derivatives And Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91:209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes Of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

PHOSPHORESCENT MATERIALS

CROSS-REFERENCE TO RELATED APPLICATIONS

This application is a divisional application of U.S. patent application Ser. No. 12/559,764, filed Sep. 15, 2009, which claims priority to U.S. Provisional Application No. 61/097,488, filed Sep. 16, 2008, the disclosures of which are expressly incorporated herein by reference in their entirety.

JOINT RESEARCH AGREEMENTS

The claimed invention was made by, on behalf of, and/or in connection with one or more of the following parties to a joint university corporation research agreement: Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and specifically to phosphorescent organic materials used in such devices. More specifically, the present invention relates to iridium compounds having a narrow spectrum incorporated into OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure of Formula I:

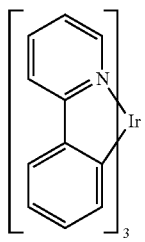

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds are provided having the formula

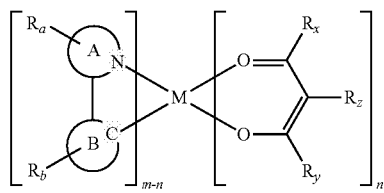

wherein M is a metal of atomic weight higher than 40; wherein A and B are each independently a 5 or 6-membered aromatic or heteroaromatic ring, and A-B represents a bonded pair of aromatic or heteroaromatic rings coordinated to the metal via a nitrogen atom on ring A and an $sp^2$ hybridized carbon atom on ring B; wherein $R_a$, $R_b$, $R_x$, $R_y$, $R_z$ are each independently selected from the group consisting of no substitution, alkyl, heteroalkyl, aryl, or heteroaryl groups; wherein each of $R_a$ and $R_b$ represent one or more substituents; wherein at least one of $R_x$ and $R_y$ contains a branched alkyl moiety with branching at a position further than the α position to the carbonyl group; wherein m is the oxidation state of the metal; and wherein n is at least 1.

The compound can be

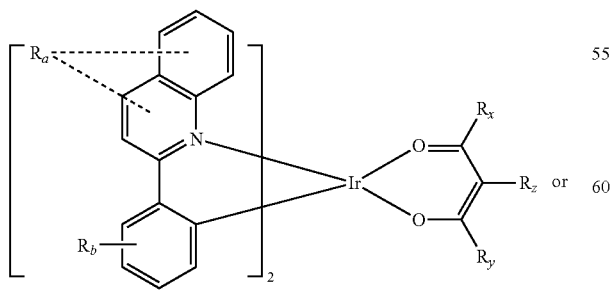

or

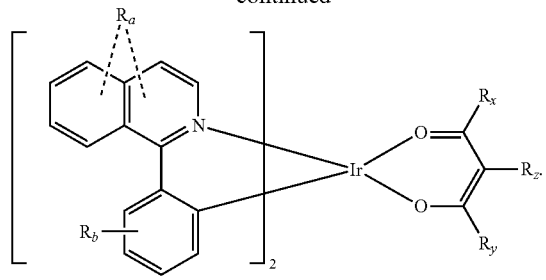

$R_x$ and $R_y$ can an isobutyl group. $R_z$ can be hydrogen.

Specific exemplary compounds are also aprovided, e.g., Compounds 3 and 5-7.

In addition, specific compounds are provided, e.g., Compounds 1, 2, 4 and 8-12.

An organic light emitting device is provided. The device comprises an anode, a cathode, and an organic layer disposed between the anode and the cathode. The organic layer comprises one or more of the inventive compounds. The organic layer can be an emissive layer that contains an emissive dopant and a host, wherein the inventive compound is the emissive dopant and BAlq is the host.

A consumer product is also provided. The consumer product comprises a device which itself comprises an anode, a cathode, and an organic layer disposed between the anode and the cathode. The organic layer comprises one or more of the inventive compounds.

A method is provided, the method comprising reacting

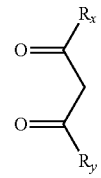

with $R_z$—X to form the free base

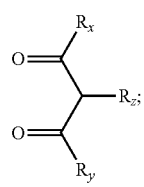

separating unreacted

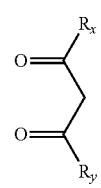

and the product

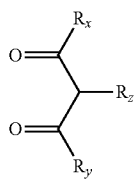

by column chromatography using a stationary phase consisting of alumina; wherein $R_x$ and $R_y$ are each independently selected from the group consisting of hydrogen, alkyl, heteroalkyl, aryl, or heteroaryl groups; wherein $R_z$ is selected from the group consisting of alkyl, heteroalkyl, aryl, or heteroaryl groups; and wherein X=Cl, Br, I, OTf, OTs or OH.

An organometallic compound is also provided, the organometallic compound containing a structure selected from the group consisting of:

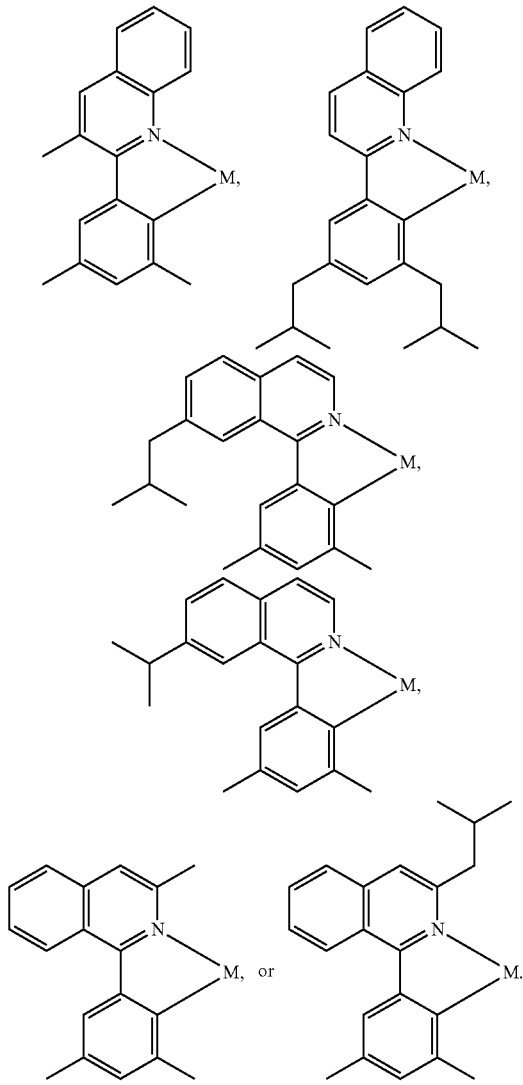

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75. No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
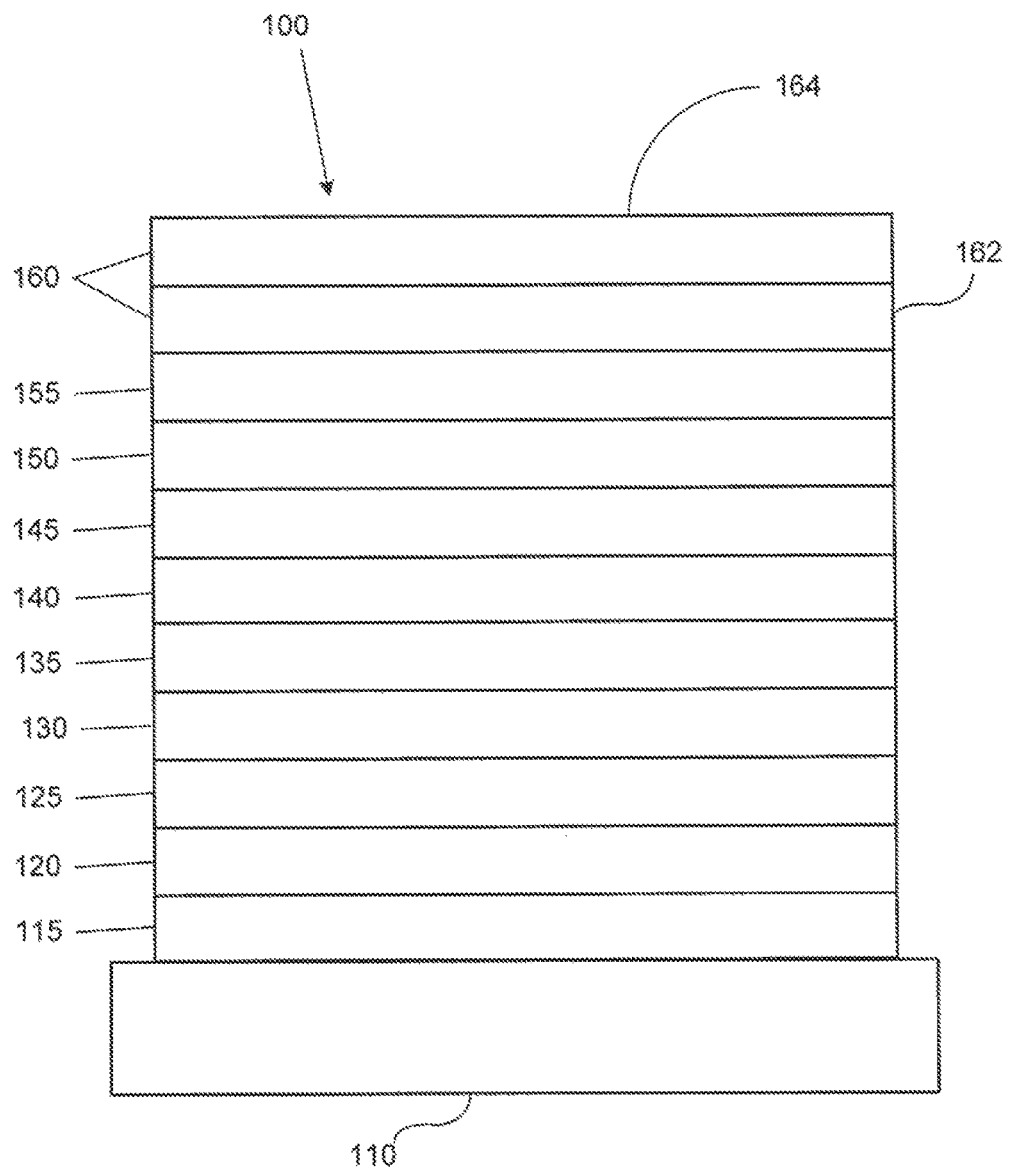
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
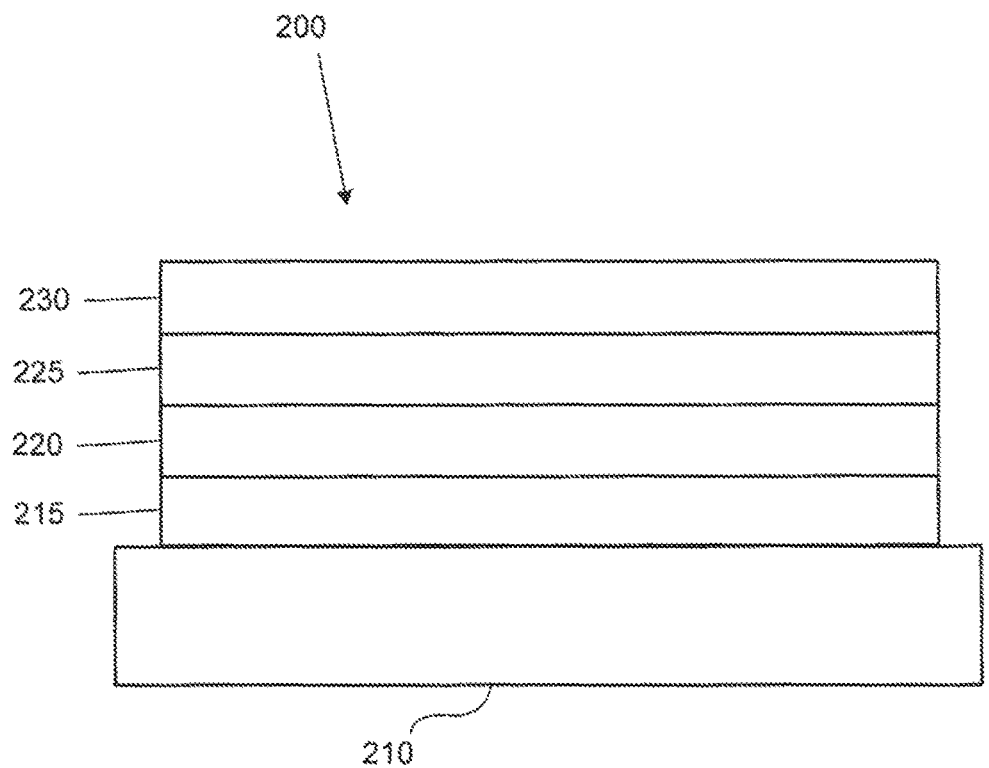
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example. OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968 to Shtein et al., which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Numerous Ir(2-phenylquinoline) and Ir(1-phenylisoquinoline) type phosphorescent materials have been synthesized, and OLEDs incorporating them as the dopant emitters have been fabricated. The devices may exhibit advantageously exhibit high current efficiency, high stability, narrow emission, improved processibility (e.g., high solubility and low sublimation temperature), and/or high luminous efficiency: quantum efficiency ratio (LE:EQE).

Using Ir(3-Meppy)3 as a base structure, different alkyl substitution patterns on both the emitting ligand and the ancillary ligand were studied to establish a structure-property relationship with respect to material processibility (evaporation temperature, evaporation stability, solubility, etc) and device characteristics of Ir(2-phenylquinoline) and Ir(1-phenylisoquinoline) type phosphorescent materials and their PHOLEDs. Alkyl substitutions are particularly important because they offer a wide range of tunability in terms of evaporation temperature, solubility, energy levels, device efficiency and narrowness of the emission spectrum. Moreover, they are stable functional groups chemically and in device operation when applied appropriately.

Figure 3:
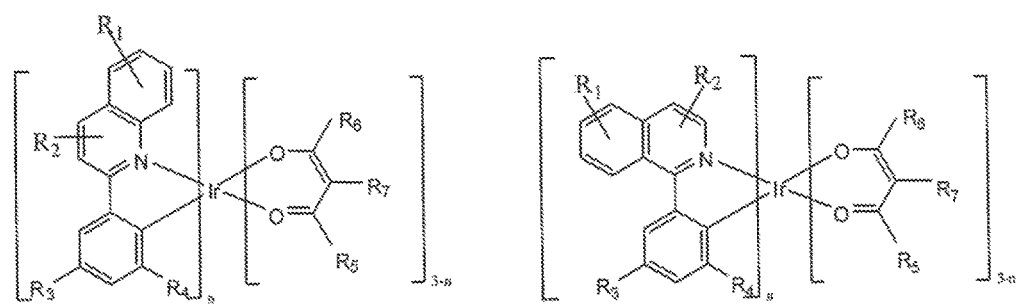
FIG. 3 shows an example of an iridium compound.

Compounds are provided, the compounds having the formula (also illustrated in FIG. 3):

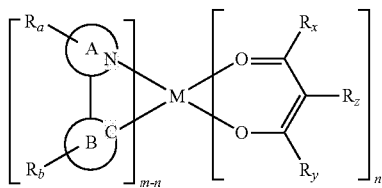

wherein M is a metal of atomic weight higher than 40; wherein A and B are each independently a 5 or 6-membered aromatic or heteroaromatic ring, and A-B represents a bonded pair of aromatic or heteroaromatic rings coordinated to the metal via a nitrogen atom on ring A and an sp2 hybridized carbon atom on ring B; wherein Ra, Rb, Rx, Ry, Rz are each independently selected from the group consisting of no substitution, alkyl, heteroalkyl, aryl, or heteroaryl groups; wherein each of $R_a$ and $R_b$ represent one or more substituents and can join to form fused rings; wherein at least one of $R_x$ and $R_y$ contains a branched alkyl moiety with branching at a position further than the α position to the carbonyl group; wherein m is the oxidation state of the metal; and wherein n is an integer less than m and at least 1.

The compound may have the formula:

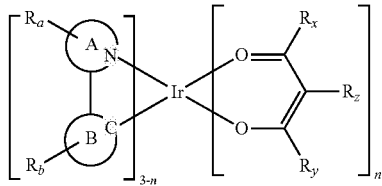

The bonded pair of aromatic or heteroaromatic rings present in the compound, represented by A-B, is selected from the group consisting of:

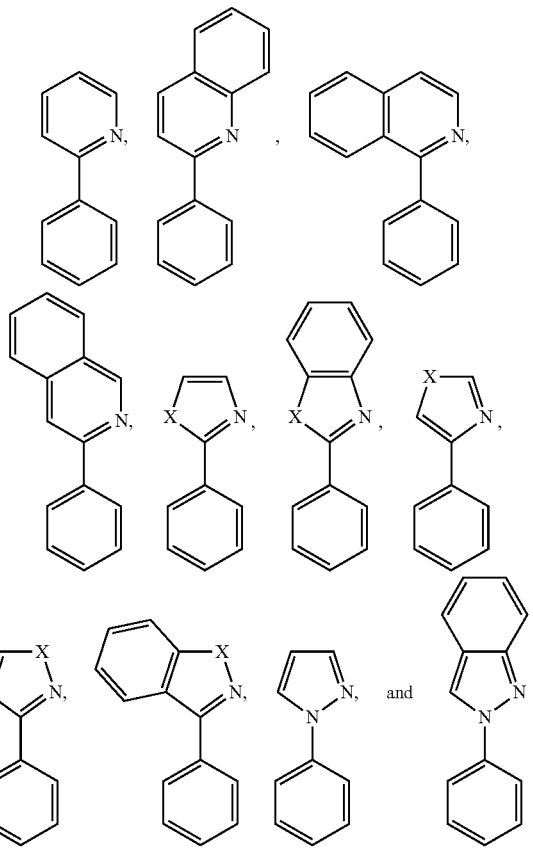

wherein X is N—R, O or S; and wherein R is selected from the group consisting of hydrogen, alkyl, heteroalkyl, aryl, and heteroaryl groups.

Additionally, the compound may have the formula:

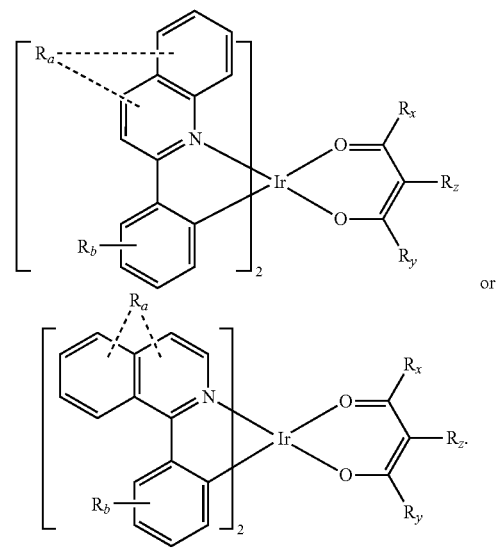

In one example, $R_x$ and $R_y$ are an isobutyl group. In another example, $R_z$ is hydrogen. Exemplary compounds include compound that are selected from the group consisting of:

Compound 3
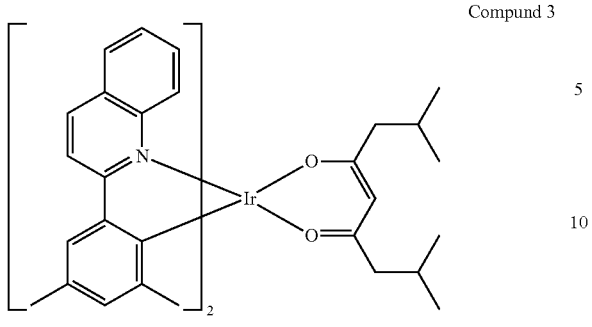

Compound 1
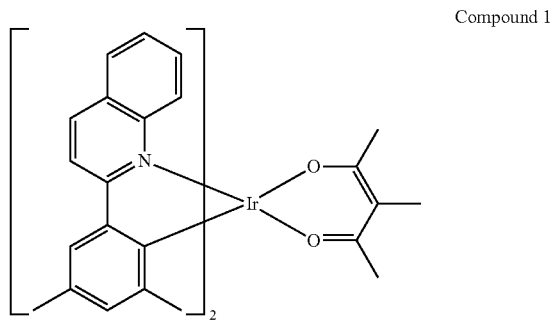

Compound 6
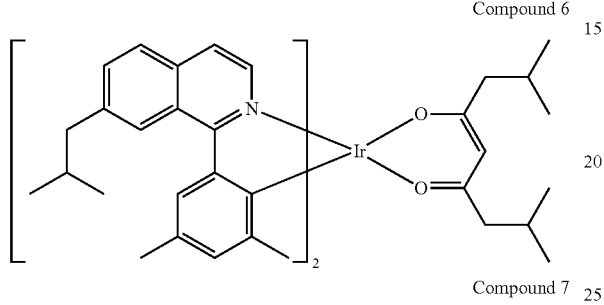

Compound 2
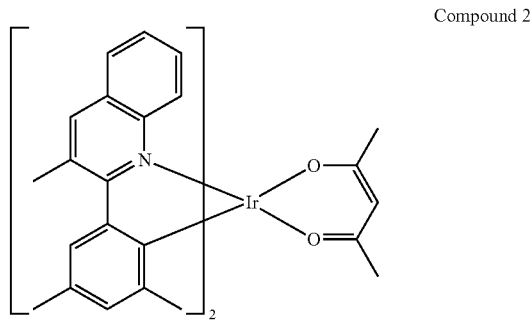

Compound 7
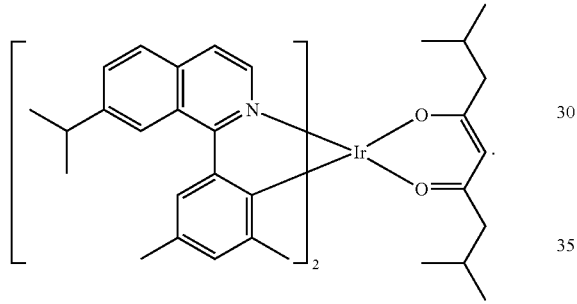

Compound 4
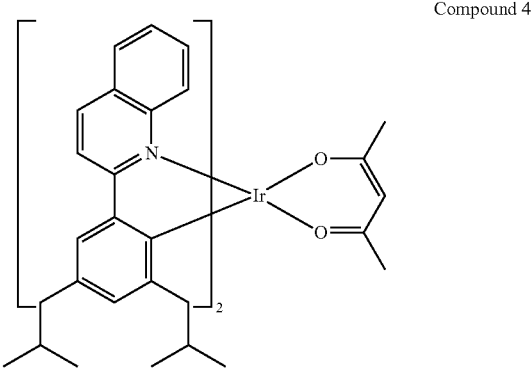

Additionally, compounds are provided wherein $R_z$ is methyl. A specific example of such a compound includes Compound 5
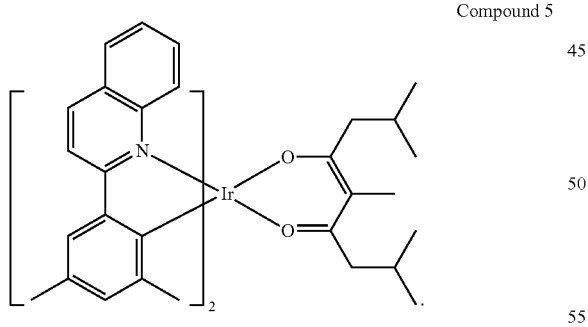

Compound 8
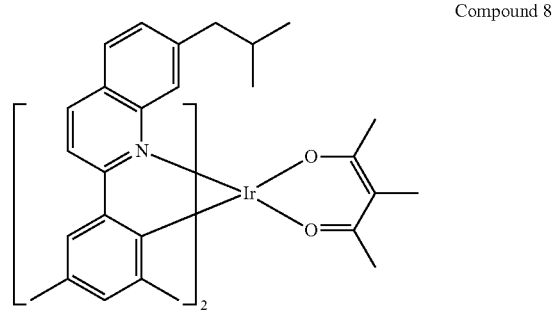

The compounds described herein provide high device efficiency and stability, and a very narrow spectrum among other desirable properties. It is thought that a branched substituents at least at one of $R_x$ and $R_y$, in combination with the methyl substituents on the phenyl ring (ring B) of the compound may provide for the very narrow emission spectrum and other remarkably good properties of the compound.

Additionally, specific compounds are provided wherein the compound is selected from the group consisting of:

Compound 9
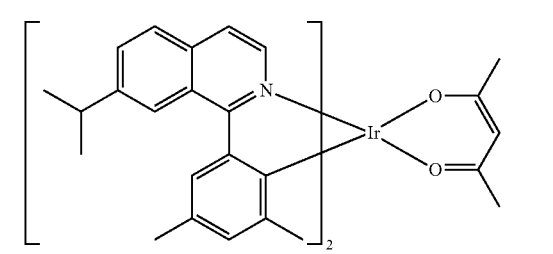

-continued

Compound 10

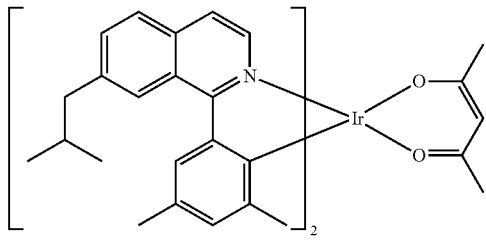

Compound 11

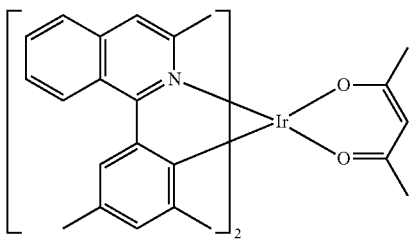

Compound 12

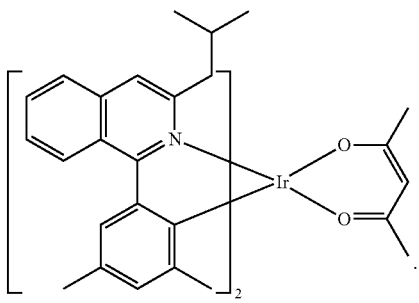

An organic light emitting device is also provided. The device comprises an anode, a cathode, and an organic layer that is disposed between the anode and the cathode. The organic layer further comprising a compound having the formula:

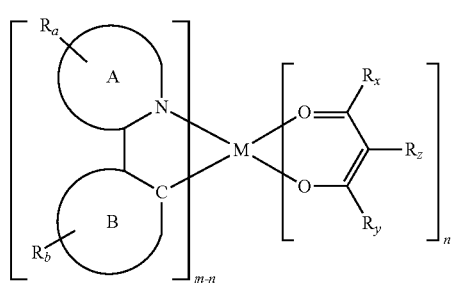

wherein M is a metal of atomic weight higher than 40; wherein A and B are each independently a 5 or 6-membered aromatic or heteroaromatic ring, and A-B represents a bonded pair of aromatic or heteroaromatic rings coordinated to the metal via a nitrogen atom on ring A and an sp² hybridized carbon atom on ring B; wherein $R_a$, $R_b$, $R_x$, $R_y$, $R_z$ are each independently selected from the group consisting of no substitution, alkyl, heteroalkyl, aryl, or heteroaryl groups; wherein each of $R_a$ and $R_b$ represent one or more substituents; wherein at least one of $R_x$ and $R_y$ contains a branched alkyl moiety with branching at a position further than the α position to the carbonyl group; wherein m is the oxidation state of the metal; and wherein n is an integer less than m and at least 1.

The device can contain the compound

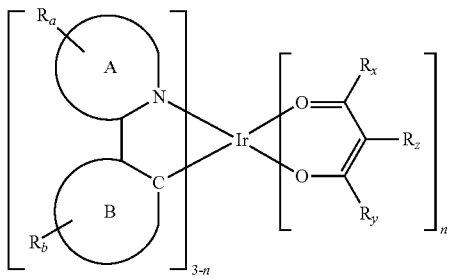

The device can contain a compound wherein A-B of the compound is selected from the group consisting of:

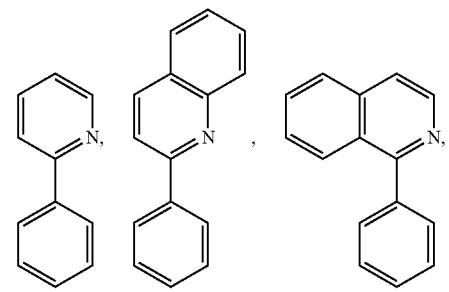

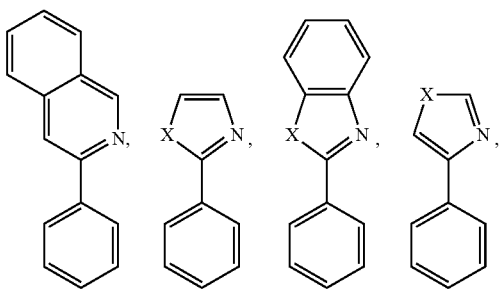

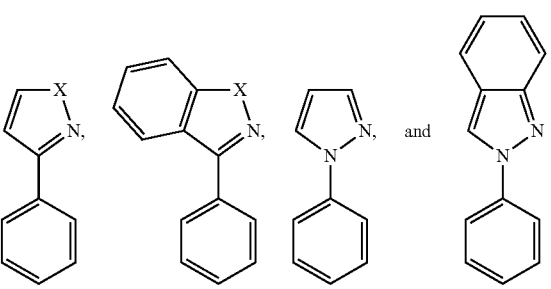

wherein X is N—R, O or S; and wherein R is selected from the group consisting of no substitution, alkyl, heteroalkyl, aryl, and heteroaryl groups.

Additionally, the device can contain a compound having the formula:

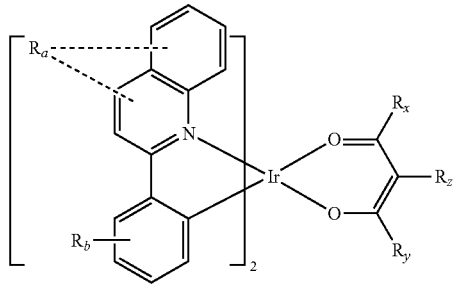

or

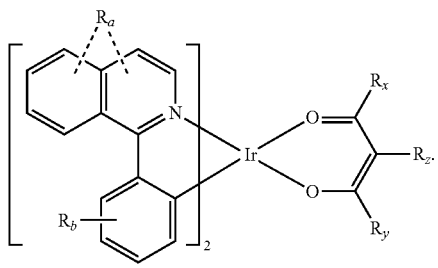

In one example, the device can contain a compound wherein $R_x$ and $R_y$ are an isobutyl group. In another example, the device can contain a compound wherein $R_z$ is hydrogen. In yet another example, the device can contain a compound selected from the group consisting of:

Compound 3

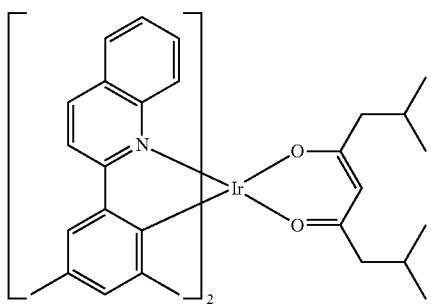

Compound 6

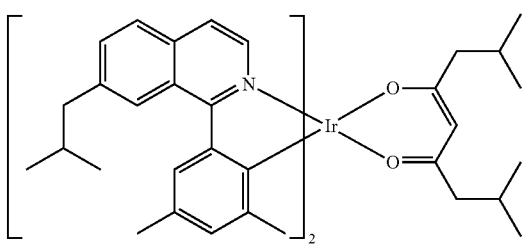

Compound 7

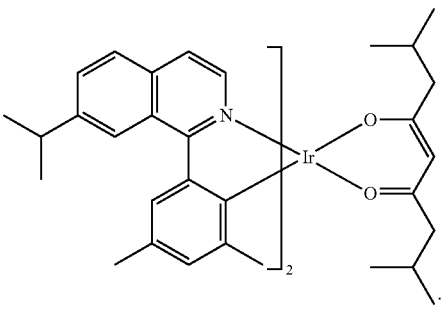

Additionally, the device can contain a compound wherein $R_z$ is methyl. Moreover, in one example, the device can contain the compound Compound 5

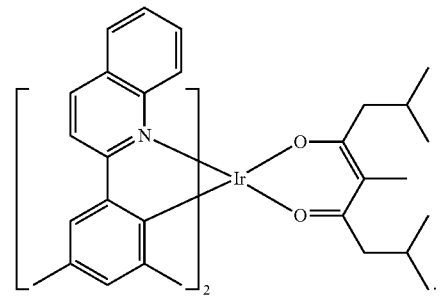

The organic layer of the device is an emissive layer comprising the compound and a host. In one example, the compound is the emissive material. In another example, the host is a metal coordination complex. The host material can be BAlq. In another example, the compound of the device is the emissive material and the host is a metal coordination complex. The host material can be BAlq.

Additionally, an organic light emitting device is provided. The device comprises an anode, a cathode, and an organic layer disposed between the anode and the cathode, the organic layer comprising a compound selected from the group consisting of:

Compound 1

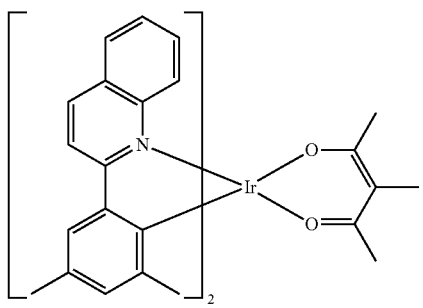

Compound 2

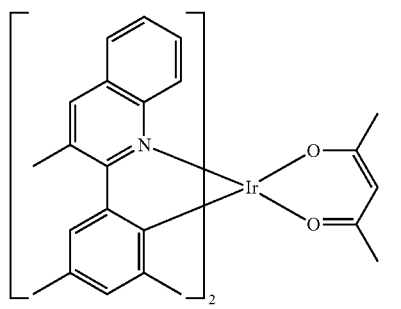

Compound 4

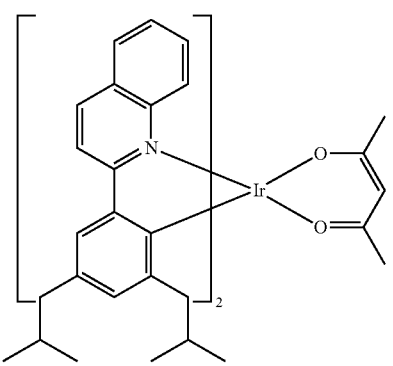

Compound 8

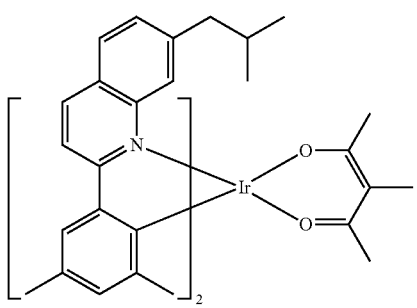

Compound 9

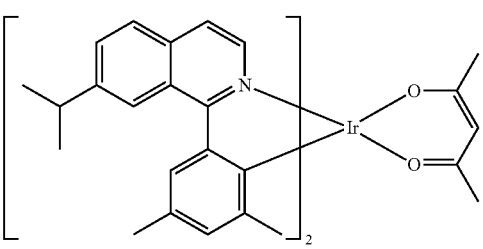

Compound 10

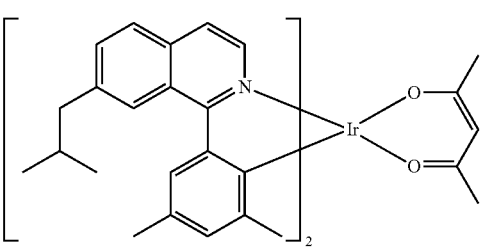

Compound 11

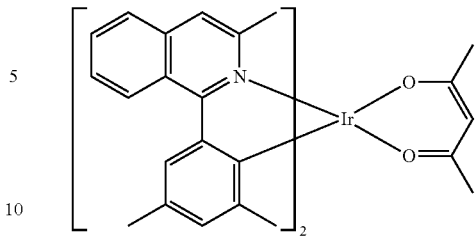

Compound 12

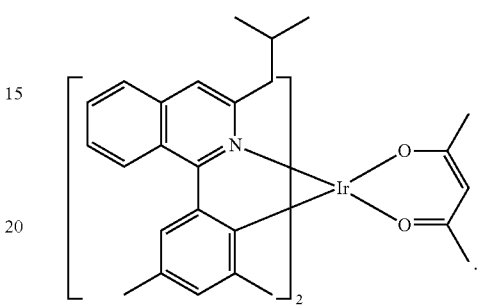

Additionally, the organic later of the device can be an emissive layer comprising the compound and a host. The inventive compound can be the emissive material and the host can be a metal coordination complex. For example, the host can be BAlq.

A consumer product is also provided. The consumer product comprising a device, the device further comprising an anode, a cathode, and an organic layer disposed between the anode and the cathode. The organic layer further comprising a compound having the formula:

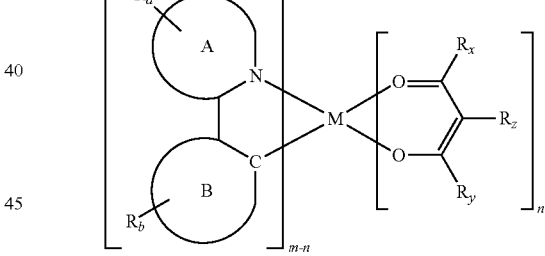

wherein M is a metal of atomic weight higher than 40; wherein A and B are each independently a 5 or 6-membered aromatic or heteroaromatic ring, and A-B represents a bonded pair of aromatic or heteroaromatic rings coordinated to the metal via a nitrogen atom on ring A and an $sp^2$ hybridized carbon atom on ring B; wherein $R_a$, $R_b$, $R_x$, $R_y$, $R_z$ are each independently selected from the group consisting of no substitution, alkyl, heteroalkyl, aryl, or heteroaryl groups; wherein each of $R_a$ and $R_b$ represent one or more substituents; wherein at least one of $R_x$ and $R_y$ contains a branched alkyl moiety with branching at a position further than the α position to the carbonyl group; wherein m is the oxidation state of the metal; and wherein n is at least 1.

Additionally, a consumer device is provided wherein the consumer product comprises a device, the device further comprising an anode, a cathode, and an organic layer disposed between the anode and the cathode. The organic layer further comprising a compound selected from the group consisting of:

Compound 1
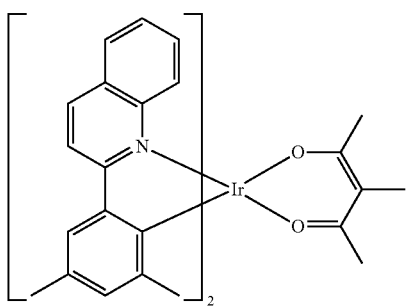
Compound 2
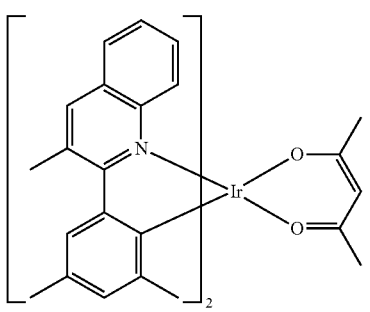
Compound 4
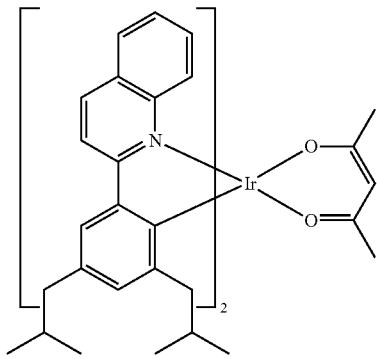
Compound 8
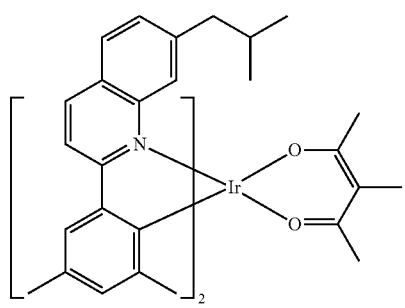
Compound 9
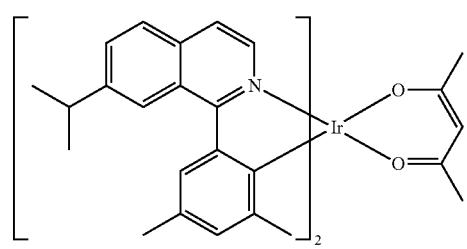
Compound 10
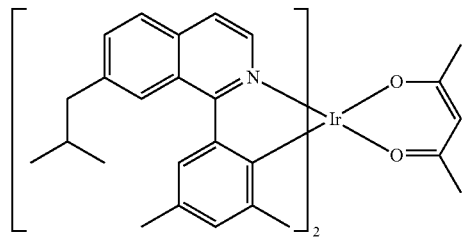
Compound 11
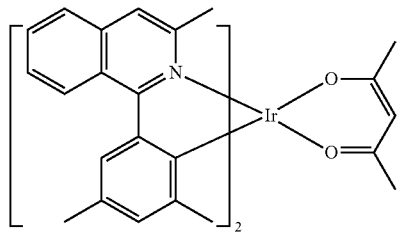
Compound 12
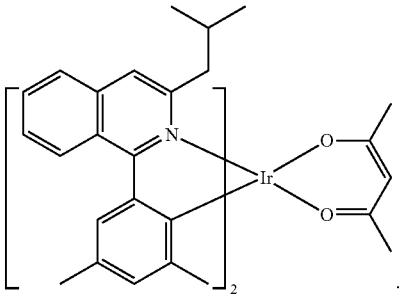
Additionally, a method is provided comprising reacting
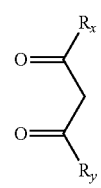
with Rz—X to form the free base
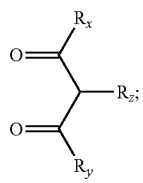

separating unreacted

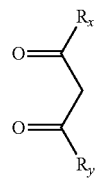

and the product

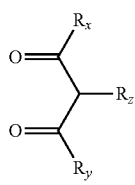

by column chromatography using a stationary phase consisting of alumina; wherein $R_x$ and $R_y$ are each independently selected from the group consisting of hydrogen, alkyl, heteroalkyl, aryl, or heteroaryl groups; wherein $R_z$ is selected from the group consisting of alkyl, heteroalkyl, aryl, or heteroaryl groups; and wherein X=Cl, Br, I, OTf, OTs or OH.

The method can further comprise reacting

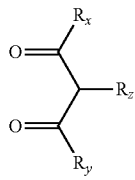

with a metal M and one or more ligands to form a compound having the formula:

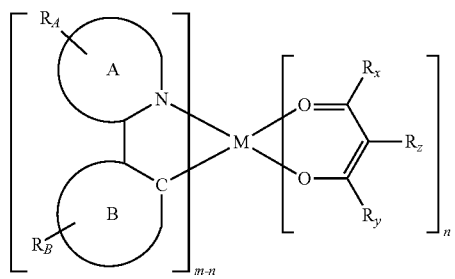

wherein M is a metal of atomic weight higher than 40; wherein A and B are each independently a 5 or 6-membered aromatic or heteroaromatic ring, and A-B represents a bonded pair of aromatic or heteroaromatic rings coordinated to the metal via a nitrogen atom on ring A and an sp² hybridized carbon atom on ring B; wherein $R_A$ and $R_B$ each represent no substitution or one or more substituents; wherein each substituent of $R_A$ and $R_B$ is independently selected from the group consisting of alkyl, heteroalkyl, aryl, or heteroaryl groups; wherein m is the oxidation state of the metal; and wherein n is an integer less than m and at least 1.

Additionally, the method can further comprise wherein $R_z$ is a methyl group; and wherein

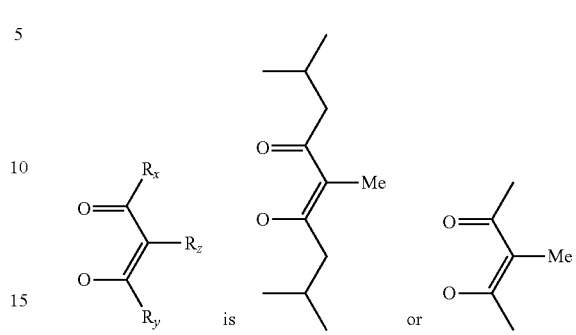

Isotopic analogues of the compounds provided herein where hydrogen has been replaced by deuterium are also included.

Additionally, an organometallic compound is provided. The organometallic compound contains a structure selected from the group consisting of

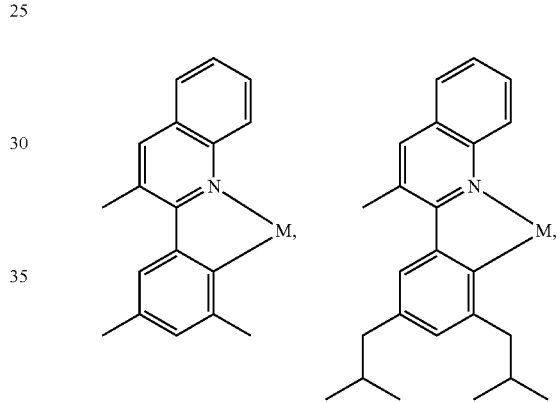

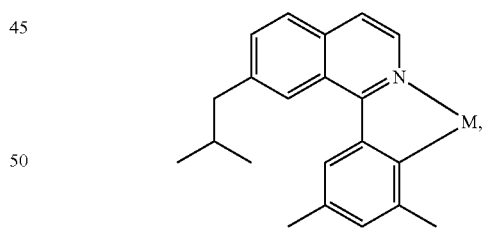

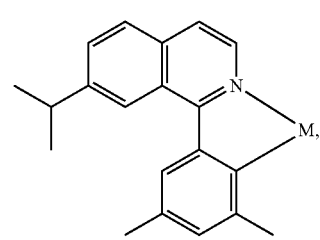

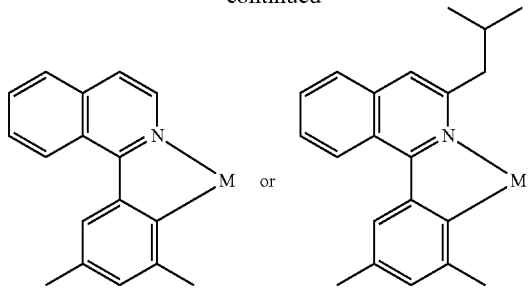

wherein M is a metal with an atomic weight greater than 40.

The organometallic compound provided can have M as Ir.

The organometallic compound provided can be a phosphorescent material.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| *Hole injection materials* | | |
| Phthalocyanine and porphryin compounds | | Appl. Phys. Lett. 69, 2160 (1996) |
| Starburst triarylamines | | J. Lumin. 72-74, 985 (1997) |
| CF$_x$ Fluorohydrocarbon polymer | $-(CH_xF_y)_n-$ | Appl. Phys. Lett. 78, 673 (2001) |

TABLE 1-continued

| MATERIAL | EXAMPLES OF MATERIAL | PUBLICATIONS |
| --- | --- | --- |
| Conducting polymers (e.g., PEDOT:PSS, polyaniline, polypthiophene) | | Synth. Met. 87, 171 (1997) |
| Arylamines complexed with metal oxides such as molybdenum and tungsten oxides | + MoO$_x$ | SID Symposium Digest, 37, 923 (2006) |

Hole transporting materials

| | | |
| --- | --- | --- |
| Triarylamines (e.g., TPD, α-NPD) | | Appl. Phys. Lett. 51, 913 (1987) |
| | | U.S. Pat. No. 5,061,569 |
| | | EP650955 |

TABLE 1-continued

| MATERIAL | EXAMPLES OF MATERIAL | PUBLICATIONS |
|---|---|---|
| | | J. Mater. Chem. 3, 319 (1993) |
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |

TABLE 1-continued

| MATERIAL | EXAMPLES OF MATERIAL | PUBLICATIONS |
|---|---|---|
| Arylamine carbazole compounds | | Adv. Mater. 6, 677 (1994) |
| Indolocarbazoles | | Synth. Met. 111, 421 (2000) |
| Isoindole compounds | | Chem. Mater. 15, 3148 (2003) |

TABLE 1-continued
| MATERIAL | EXAMPLES OF MATERIAL | PUBLICATIONS |
|---|---|---|
| | Phosphorescent OLED host materials | |
| | Red hosts | |
| Arylcarbazoles | 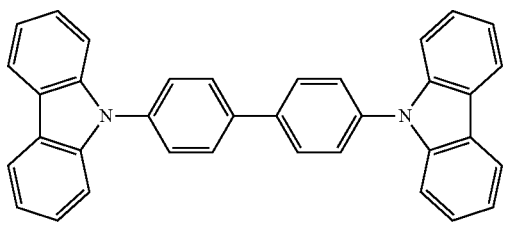 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., $Alq_3$, BAlq) | 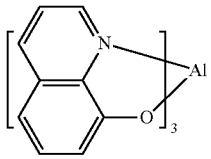 | Nature 395, 151 (1998) |
| | 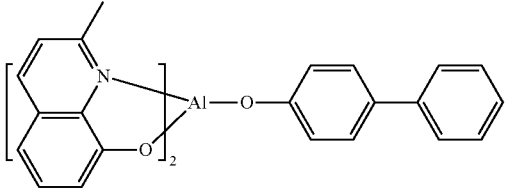 | US20060202194 |
| | 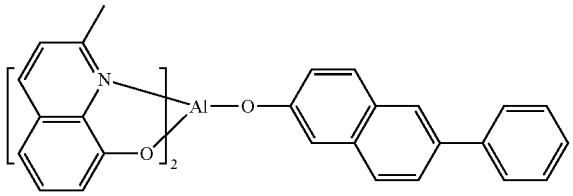 | WO2005014551 |
| Metal phenoxybenzothiazole compounds | 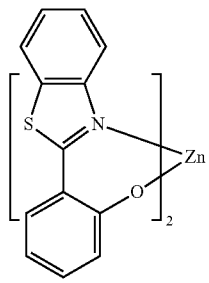 | Appl. Phys. Lett. 90, 123509 (2007) |
| Conjugated oligomers and polymers (e.g., polyfluorene) | 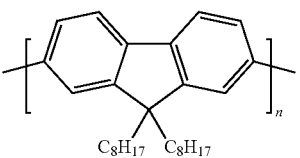 | Org. Electron. 1, 15 (2000) |
| | Green hosts | |
| Arylcarbazoles | 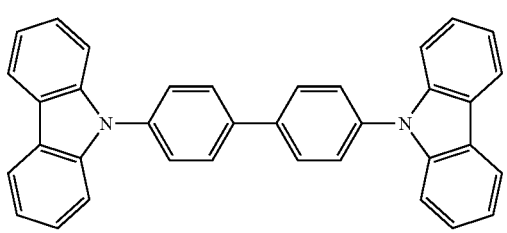 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

| MATERIAL | EXAMPLES OF MATERIAL | PUBLICATIONS |
|---|---|---|
| | 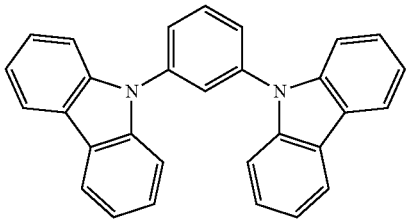 [SMILES: c1cc(-n2c3ccccc3c3ccccc32)cc(-n2c3ccccc3c3ccccc32)c1] | US20030175553 |
| | 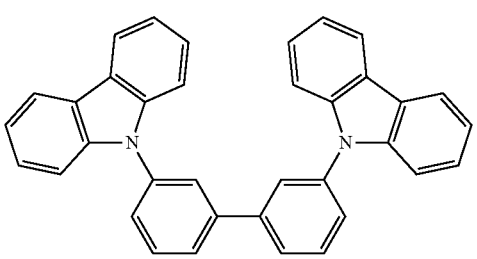 [SMILES: c1cc(-c2cccc(-n3c4ccccc4c4ccccc43)c2)cc(-n2c3ccccc3c3ccccc32)c1] | WO2001039234 |
| Aryltriphenylene compounds | 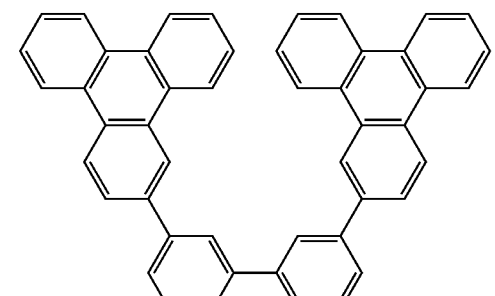 | US20060280965 |
| | 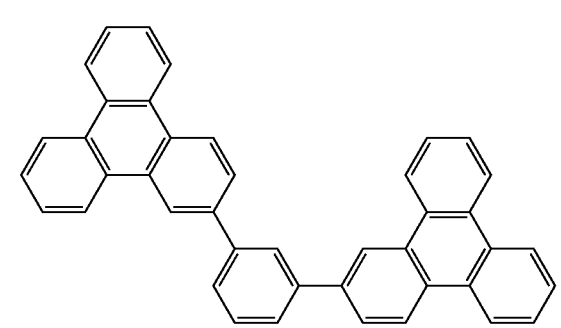 [SMILES: c1cc(-c2ccc3c4ccccc4c4ccccc4c3c2)cc(-c2ccc3c4ccccc4c4ccccc4c3c2)c1] | US20060280965 |
| Polymers (e.g., PVK) | 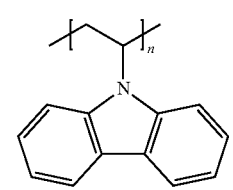 | Appl. Phys. Lett. 77, 2280 (2000) |
| Spirofluorene compounds | 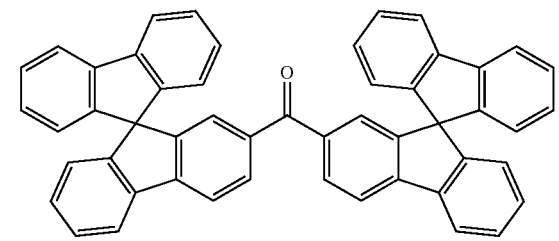 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 1-continued

| MATERIAL | EXAMPLES OF MATERIAL | PUBLICATIONS |
|---|---|---|
| Metal phenoxy-benzooxazole compounds | | WO05089025 |
| | | WO06132173 |
| | | JP200511610 |
| Spirofluorene-carbazole compounds | | JP2007254297 |
| | | JP2007254297 |

TABLE 1-continued

| MATERIAL | EXAMPLES OF MATERIAL | PUBLICATIONS |
| --- | --- | --- |
| Indolocarbazoles | | WO07063796 |
| | | WO07063754 |
| 5-member ring electron deficient heterocycles (e.g., triazole, oxadiazole) | | J. Appl. Phys. 90, 5048 (2001) |
| | | WO04107822 |
| Metal phenoxypyridine compounds | | WO05030900 |
| Blue hosts | | |
| Arylcarbazoles | | Appl. Phys. Lett, 82, 2422 (2003) |

| MATERIAL | EXAMPLES OF MATERIAL | PUBLICATIONS |
|---|---|---|
| | 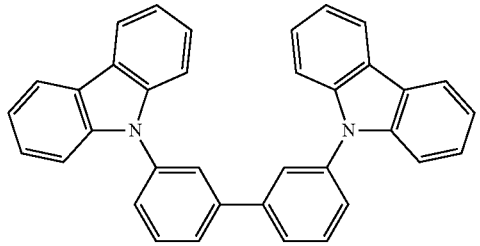 [SMILES: c1cc(-c2cccc(-n3c4ccccc4c4ccccc43)c2)cc(-n2c3ccccc3c3ccccc32)c1] | US20070190359 |
| Dibenzothiophene/ carbazole compounds | 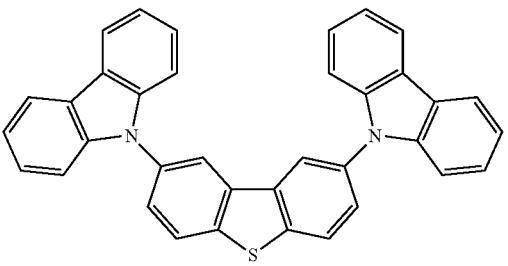 [SMILES: c1ccc2c(c1)c1ccccc1n2-c1ccc2sc3ccc(-n4c5ccccc5c5ccccc54)cc3c2c1] | WO2006114966 |
Phosphorescent dopants
Red dopants
| Heavy metal porphyrins (e.g., PtOEP) | 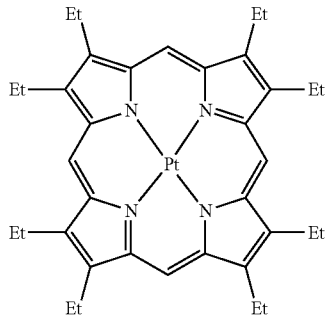 | Nature 395, 151 (1998) |
|---|---|---|
| Iridium(III) organometallic complexes | 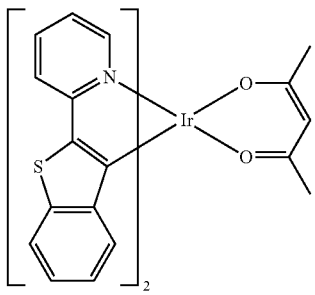 | Appl. Phys. Lett. 78, 1622 (2001) |
| | 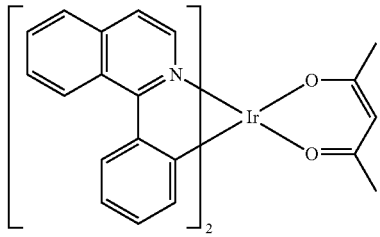 | US06835469 |

TABLE 1-continued

| MATERIAL | EXAMPLES OF MATERIAL | PUBLICATIONS |
| --- | --- | --- |
| | | US06835469 |
| | | US20060202194 |
| | | US20060202194 |
| | | US070087321 |
| | | US070087321 |

TABLE 1-continued

| MATERIAL | EXAMPLES OF MATERIAL | PUBLICATIONS |
|---|---|---|
|  | [Ir complex with isoquinoline ligand, C8H17 substituent] | Adv. Mater. 19, 739 (2007) |
| Platinum(II) organometallic complexes | [Pt complex with isoquinoline and acac ligands] | WO2003040257 |
| Osmium(III) complexes | [Os(PPhMe$_2$)$_2$ complex with CF$_3$-pyrazole/pyridine ligand] | Chem. Mater. 17, 3532 (2005) |
| Ruthenium(II) complexes | [Ru(PPhMe$_2$)$_2$ complex with tBu-pyrazole/isoquinoline ligand] | Adv. Mater. 17, 1059 (2005) |

Green dopants

| | | |
|---|---|---|
| Iridium(III) organometallic complexes | [Ir(ppy)$_3$] and its derivatives | Inorg. Chem. 40, 1704 (2001) |

TABLE 1-continued
| MATERIAL | EXAMPLES OF MATERIAL | PUBLICATIONS |
|---|---|---|
| | 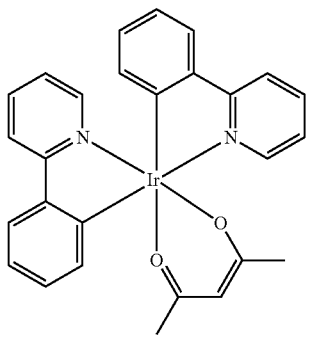 | US20020034656 |
| | 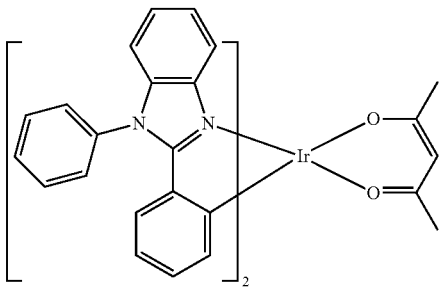 | US06687266 |
| | 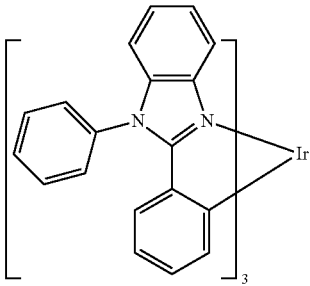 | Chem. Mater. 16, 2480 (2004) |
| | 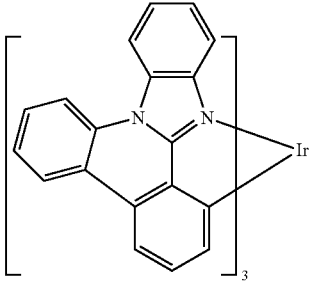 | US2007190359 |
| | 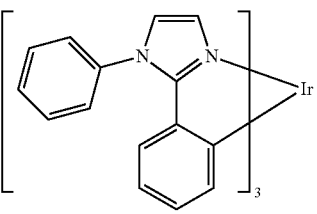 | US 20060008670<br>JP2007123392 |

TABLE 1-continued

| MATERIAL | EXAMPLES OF MATERIAL | PUBLICATIONS |
|---|---|---|
|  |  | Adv. Mater. 16, 2003 (2004) |
|  |  | Angew. Chem. Int. Ed. 2006, 45, 7800 |
| Pt(II) organometallic complexes |  | Appl. Phys. Lett. 86, 153505 (2005) |
|  |  | Appl. Phys. Lett. 86, 153505 (2005) |
|  |  | Chem. Lett. 34, 592 (2005) |

TABLE 1-continued

| MATERIAL | EXAMPLES OF MATERIAL | PUBLICATIONS |
|---|---|---|
| Gold complexes | | Chem. Commun. 2906 (2005) |
| Rhenium(III) complexes | | Inorg. Chem. 42, 1248 (2003) |
| Blue dopants | | |
| Iridium(III) organometallic complexes | | WO2002002714 |
| | | WO2006009024 |
| | | US20060251923 |
| | | WO2006056418, US20050260441 |

TABLE 1-continued

| MATERIAL | EXAMPLES OF MATERIAL | PUBLICATIONS |
|---|---|---|
| | | US20070190359 |
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |
| | | WO05123873 |

TABLE 1-continued

| MATERIAL | EXAMPLES OF MATERIAL | PUBLICATIONS |
| --- | --- | --- |
| | | WO05123873 |
| | | WO07004380 |
| | | WO06082742 |
| Osmium(II) complexes | | US2005260449 |
| | | Organometallics 23, 3745 (2004) |
| Gold complexes | | Appl. Phys. Lett. 74, 1361 (1999) |

TABLE 1-continued

| MATERIAL | EXAMPLES OF MATERIAL | PUBLICATIONS |
| --- | --- | --- |
| Platinum(II) complexes | | WO06098120, WO06103874 |

Exciton/hole blocking layer materials

| | | |
| --- | --- | --- |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 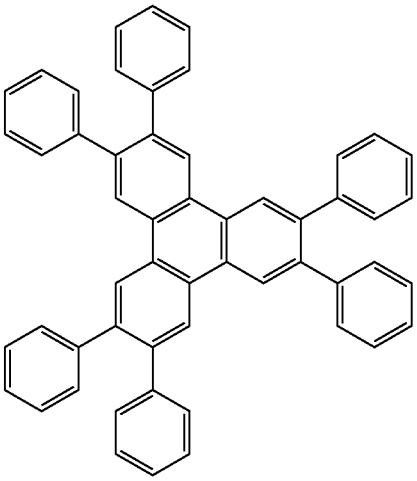 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 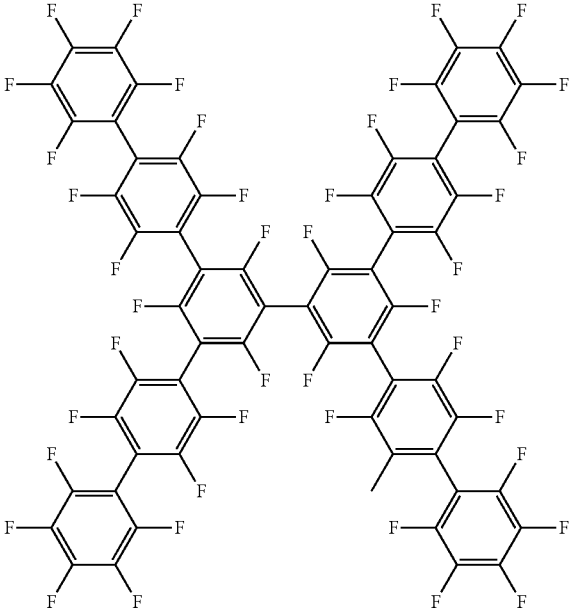 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
Electron transporting materials TABLE 1-continued

| MATERIAL | EXAMPLES OF MATERIAL | PUBLICATIONS |
| --- | --- | --- |
| Anthracene-benzoimidazole compounds | | WO03060956 |
| Anthracene-benzothiazole compounds | | Appl. Phys. Lett. 89, 063504 (2006) |
| Metal 8-hydroxyquinolates (e.g., Alq$_3$) | | Appl. Phys. Lett. 51, 913 (1987) |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 1-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 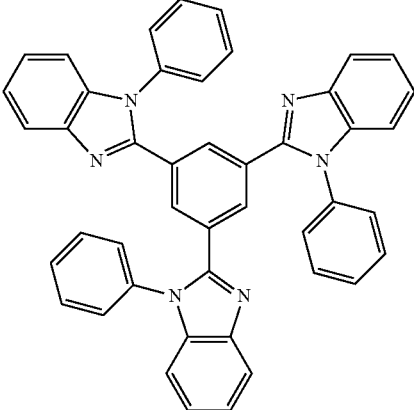 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 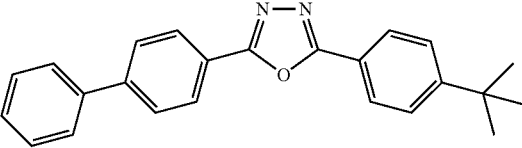 [SMILES: CC(C)(C)c1ccc(-c2nnc(-c3ccc(-c4ccccc4)cc3)o2)cc1] | Appl. Phys. Lett. 55, 1489 (1989) |
| | 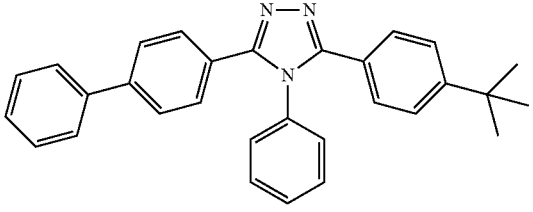 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 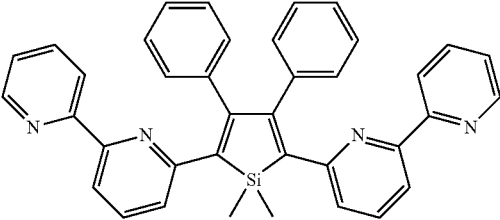 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 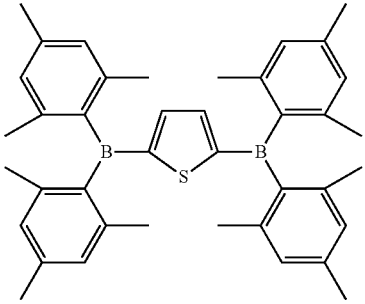 | J. Am. Chem. Soc. 120, 9714 (1998) |
| Fluorinated aromatic compounds | 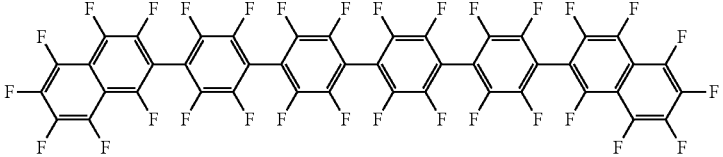 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

EXPERIMENTAL

Compound Examples

Synthesis of Compound 1

Step 1

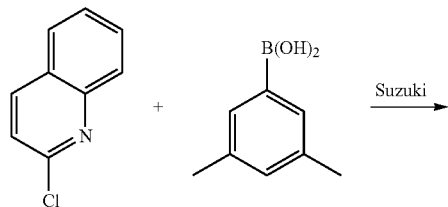

2-chloroquinoline (9.0 g, 54.4 mmol), 3,5-dimethylphenylboronic acid (9.2 g, 59.8 mmol), Pd(PPh3)$_4$ (1.8 g, 1.5 mmol), K$_2$CO$_3$ (22.4 g, 163 mmol), 1,2-dimethoxyethane (150 mL) and water (150 mL) were charged in a 500 mL round bottom flask. The reaction mixture was heated to reflux under nitrogen for 18 h. The reaction mixture was then cooled to ambient and the organic phase was separated from the aqueous phase. The aqueous phase was washed with ethyl acetate and all the organic components were combined and dried over anhydrous magnesium sulphate. The solvent was then removed under vacuum and the product was purified using silica gel chromatography (10% ethyl acetate in hexane as eluent). The material obtained was further purified by vacuum distillation to yield 12.2 g (95% yield) of product as a colorless oil.

Step 2

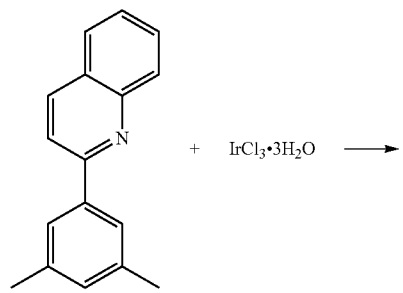

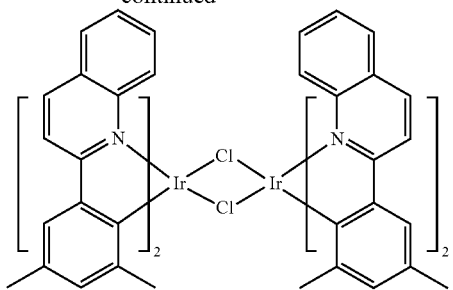

The ligand from step 1 (46 g, 197.4 mmol), 2-ethoxyethanol (536 mL) and water (178 mL) were charged in a 1 L three-neck round bottom flask. Nitrogen gas was bubbled through the reaction mixture 45 min. IrCl$_3$.H$_2$O (32.0 g 86.2 mmol) was then added and the reaction mixture was heated to reflux under nitrogen for 17 hours. The reaction mixture was cooled to ambient and filtered. The dark gray residue was washed with methanol (4×150 mL) followed by hexanes (3×300 mL). 36.5 gram of the dichlorobridged Iridium dimer was obtained after drying in vacuum oven.

Step 3

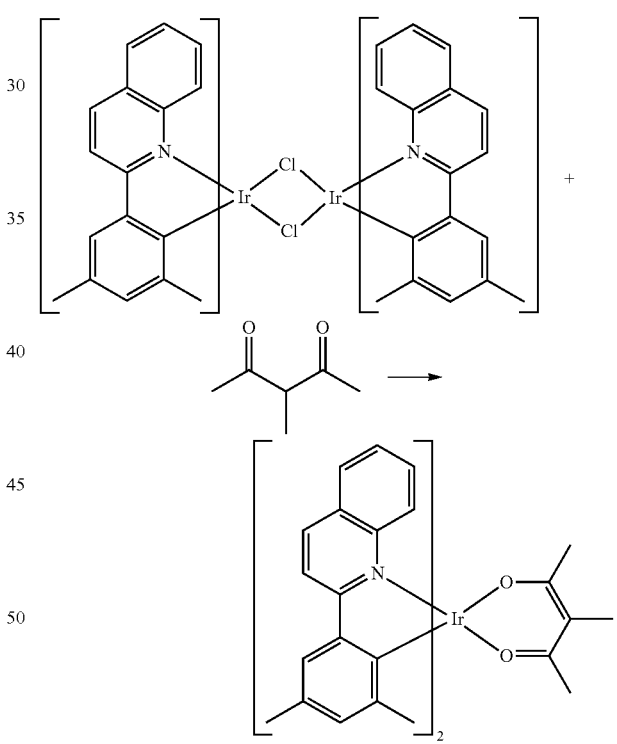

Dichlorobridged Iridium dimer from step 2 (3.0 g, 2.2 mmol), 10 mol eq 3-methyl-2,4-pentanedione (2.5 g,), 20 mol eq of Na$_2$CO$_3$ (6.3 g) and 25 mL of 2-ethoxyethanol were placed in a 250 mL round bottom flask. The reaction mixture was stirred at ambient for 24 hours. 2 g of celite and 200 mL of dichloromethane was added to the reaction mixture to dissolve the product. The mixture was then filtered through a bed of celite. The filtrate was then passed through a through a silica/alumina plug and washed with dichloromethane. The clarified solution was then filtered through GF/F filter paper the filtrate was heated to remove most of the dichloromethane. 20 mL of isopropanol was then added and the slurry was cooled to ambient and the product was filtered and washed with isopropanol and dried to give 3.2 g of crude product(97% yield). This product was then recrystallised twice using dichloromethane and isopropanol and then sublimed.

Synthesis of Compound 2

Step 1

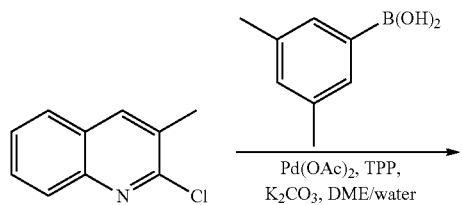

2-chloro-3-methyl-quinoline (4.5 g, 25.0 mmol), dimethylphenylboronic acid (4.6 g, 30 mmol), triphenylphosphine (1.60 g, 6.11 mmol), and potassium carbonate (12.67 g, 91.69 mmol) were charged in a 250 mL round bottom flask. 25 mL water and 25 mL of dimethoxyethane was added to the flask. Nitrogen was bubbled through the reaction mixture for 30 min. Palladium acetate (0.34 g, 1.53 mmol) was then added to the reaction mixture was then refluxed overnight under an atmosphere of nitrogen. The product was extracted with ethyl acetate, washed with water, and dried over anhydrous magnesium sulfate. The product was purified using silica gel chromatography (5-15% ethyl acetate in hexane as eluent) to give a light yellow oil(85% yield). Further purification was done via vacuum distillation Step 2

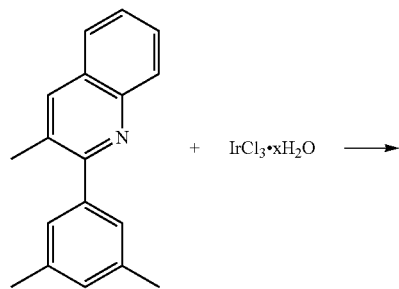

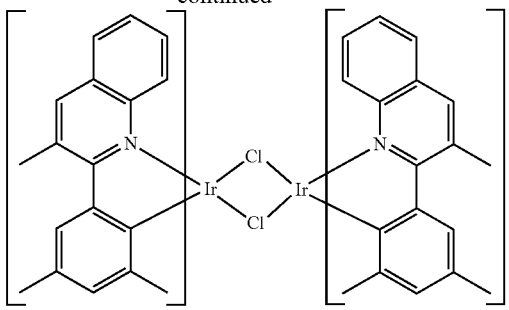

Ligand from step 1 (16 g, 65 mmol), iridium chloride (5.0 g, 14 mmol), 2-ethoxyethanol (75 mL) and water (12.5 mL) was charged in a 250 mL round bottom flask. The reactor contents were heated to 102° C. under an atmosphere of nitrogen for 16-19 h. The dichloro iridium bridged dimer was not isolated.

Step 3

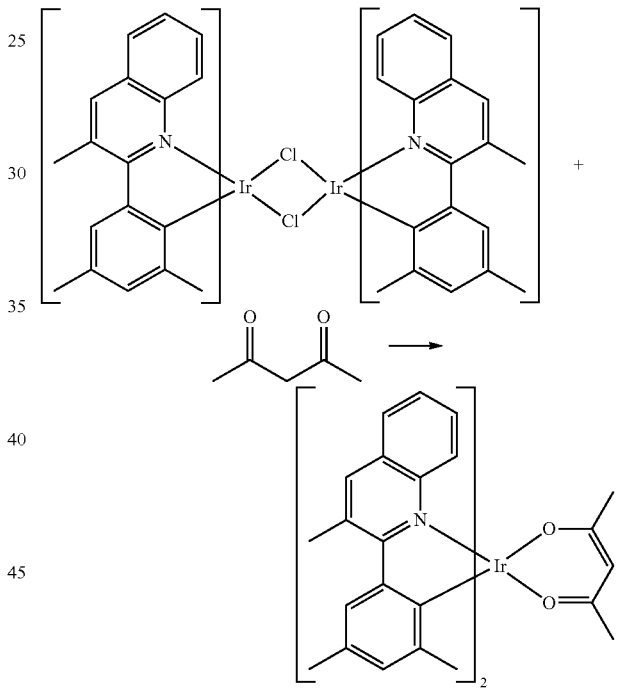

The reactor contents from step 2 were cooled to anmbient. 2,4-pentanedione (14.0 g 140 mmol) and sodium carbonate (30.0 g, 280 mmol) were added to the reactor. The reaction mixture was stirred at ambient for 24 h. 5 g of celite and 500 mL of dichloromethane was added to the reaction mixture to dissolve the product. The mixture was then filtered through a bed of celite. The filtrate was then passed through a through a silica/alumina plug and washed with dichloromethane. The clarified solution was then filtered through GF/F filter paper the filtrate was heated to remove most of the dichloromethane. 20 mL of isopropanol was then added and the slurry was cooled to ambient and the product was filtered and washed with isopropanol and dried to give 6.3 g of crude product(57% yield). This product was then recrystallised twice using dichloromethane and isopropanol and then sublimed.

Synthesis of Compound 3

Step 1

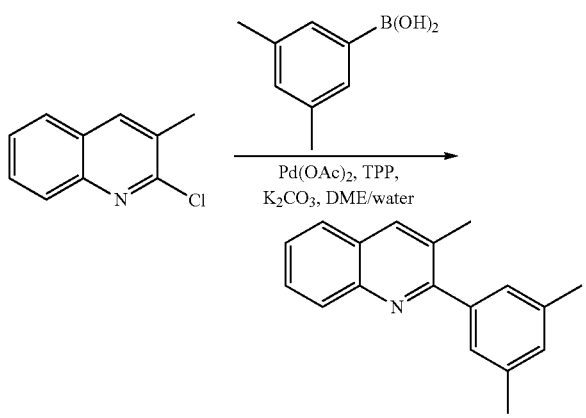

2-chloroquinoline (9.0 g, 54.4 mmol), 3,5-dimethylphenylboronic acid (9.2 g, 59.8 mmol), Pd(PPh3)$_4$ (1.8 g, 1.5 mmol), K$_2$CO (22.4 g, 163 mmol), 1,2-dimethoxyethane (150 mL) and water (150 mL) were charged in a 500 mL round bottom flask. The reaction mixture was heated to reflux under nitrogen for 18 h. The reaction mixture was then cooled to ambient and the organic phase was separated from the aqueous phase. The aqueous phase was washed with ethyl acetate and all the organic components were combined and dried over anhydrous magnesium sulphate. The solvent was then removed under vacuum and the product was purified using silica gel chromatography (10% ethyl acetate in hexane as eluent). The material obtained was further purified by vacuum distillation to yield 12.2 g (95% yield) of product as a colorless oil.

Step 2

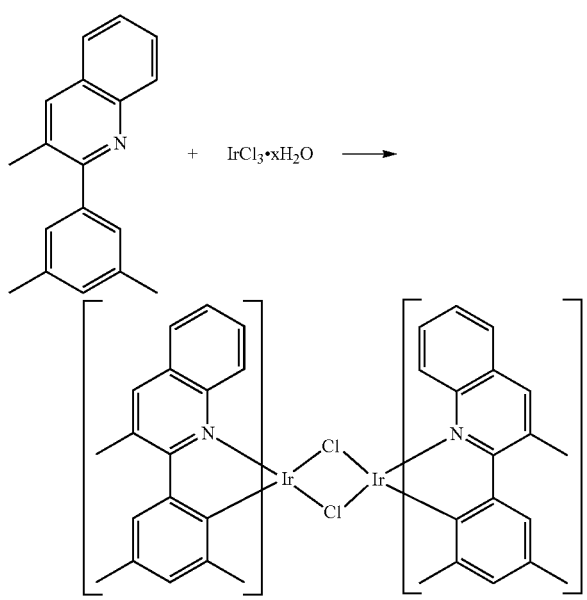

The ligand from step 1 (46 g, 197.4 mmol), 2-ethoxyethanol (536 mL) and water (178 mL) were charged in a 1 L three-neck round bottom flask. Nitrogen gas was bubbled through the reaction mixture 45 min. IrCl$_3$.H$_2$O (32.0 g 86.2 mmol) was then added and the reaction mixture was heated to reflux under nitrogen for 17 hours. The reaction mixture was cooled to ambient and filtered. The dark gray residue was washed with methanol (4×150 mL) followed by hexanes (3×300 mL). 36.5 gram of the dichlorobridged Iridium dimer was obtained after drying in vacuum oven.

Step 3

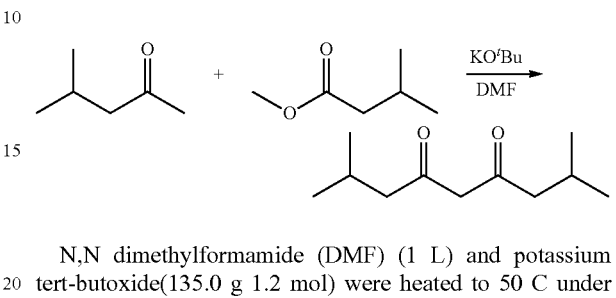

N,N dimethylformamide (DMF) (1 L) and potassium tert-butoxide(135.0 g 1.2 mol) were heated to 50 C under nitrogen. Methyl 3-methylbutanoate (86.0 g, 0.75 mol) was added dropwise from a dropping funnel followed by a solution of 4-methylpentane-2-one(50 g, 1 mol) in 100 mL DMF. The progress of the reacrtion ws monitored by GC. When the reaction was completed, the mixture was cooled to ambient and slowly neutralized with 20% H2SO4 solution. Water (300 mL) was added and two layers formed. The layer containing the 2,8-dimethylnonane-4,6-dione was purified using vacuum distillation to give 40 g of a pink oil (43% yield)

Step 4

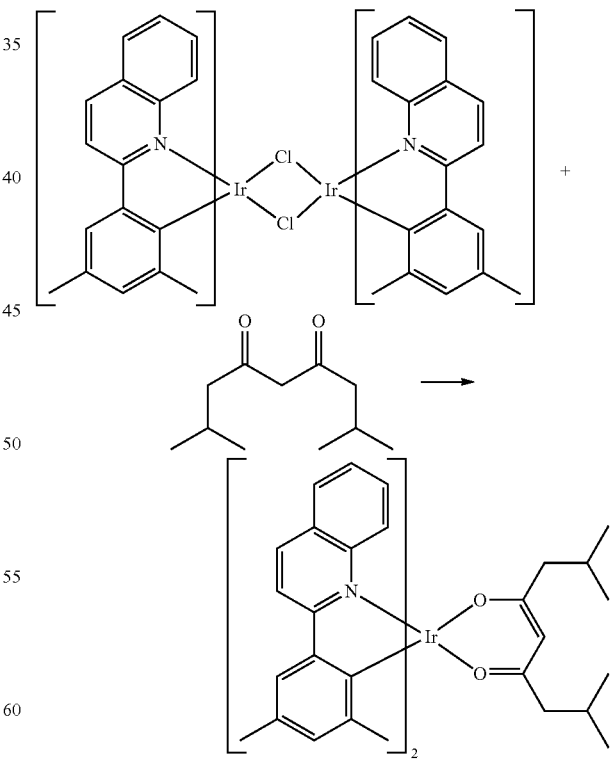

Dichlorobridged Iridium dimer from step 2 (3.0 g, 2.2 mmol), 10 mol eq 2,8-dimethylnonane-4,6-dione (4.1 g,), 20 mol eq of Na$_2$CO$_3$ (6.3 g) and 25 mL of 2-ethoxyethanol were placed in a 250 mL round bottom flask. The reaction mixture was stirred at ambient for 24 hours. 2 g of celite and 200 mL of dichloromethane was added to the reaction mixture to dissolve the product. The mixture was then filtered through a bed of celite. The filtrate was then passed through a through a silica/alumina plug and washed with dichloromethane. The clarified solution was then filtered through GF/F filter paper the filtrate was heated to remove most of the dichloromethane. 20 mL of isopropanol was then added and the slurry was cooled to ambient and the product was filtered and washed with isopropanol and dried to give 2.9 g of crude product (79% yield). This product was then recrystallised twice using dichloromethane and isopropanol and then sublimed.

Synthesis of Compound 4

Step 1

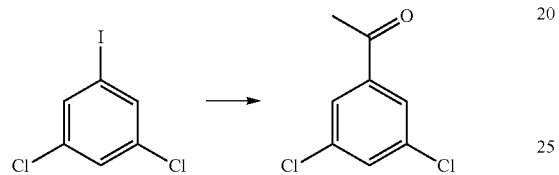

Dichloroiodobenzene (37.0 g 136 mmol), Pd$_2$(dba)$_3$(1.5 g, 1.6 mmol), Lithium chloride (29.0 g, 682 mmol) was dissolved in 100 mL of DMF in a 500 mL round bottom flask. 64.0 mL of acetic anhydride and 47.0 mL of N-Ethyldiisopropylamine was then added to the reaction mixture. The reaction was heated to 100° C. for 8 hours. Water was added to the reaction mixture and the product was extracted with ethylacetate and chromatographed using a silica gel column with ethyl acetate and hexanes as the eluent. 8 g of product was obtained.

Step 2

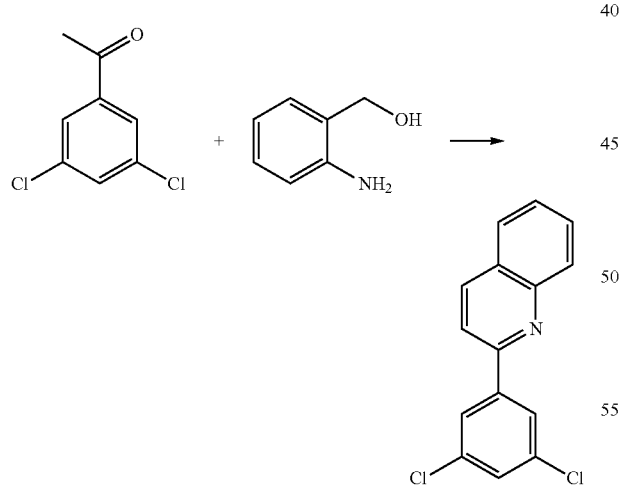

2-aminobenzyl alcohol (6.0 g, 48 mmol), 3,5-dichloroacetophenone (12.0 g, 63.5 mmol), RuCl$_2$(PPh$_3$)$_3$(0.5 g 10 mol %), and KOH (2.4 g, 42.0 mmol) was refluxed in 100 ml of toluene for 10 hours. Water was collected from the reaction using a Dean-Stark trap. The reaction mixture was allowed to cool to room temperature and filtered through a silica gel plug. The product was further purified with a silica gel column using 2% ethyl acetate in hexanes as the eluent. 4.0 g product was obtained after column (30% yield). The product was further recrystallized from isopropanol. 3.5 g of desired product was obtained.

Step 3

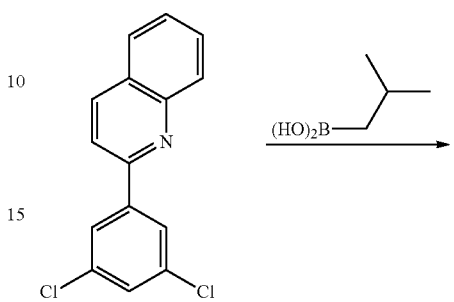

2-(3,5-dichlorophenyl)quinoline (4.0 g, 14.6 mmol), isobutylboronic acid (6.0 g, 58.4 mol), Pd$_2$(dba)$_3$(0.13 g, 1 mol %), dicyclohexylphosphino-2',6'-dimethoxybiphenyl (0.24, 4 mol %), potassium phosphate monohydrate (10 g, 13.8 mmolmol) was mixed in 100 mL of toluene in a 250 mL round bottom flask. Nitrogen was bubbled through the mixture for 20 minutes and the mixture refluxed in a nitrogen atmosphere overnight. The reaction mixture was allowed to cool and the solvent removed under vacuum. The crude product was chromatographed using a silica gel column with 2% ethyl acetate in hexanes as the eluent. The solvent was then removed under vacuo to give 3.5 g of product.

Step 4

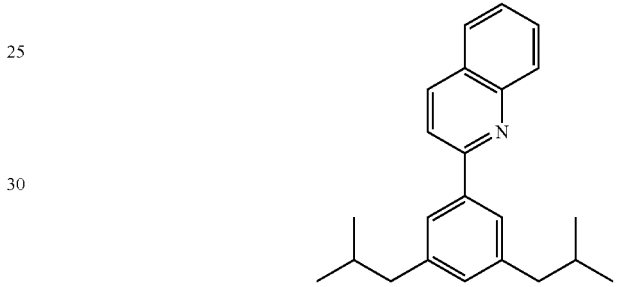

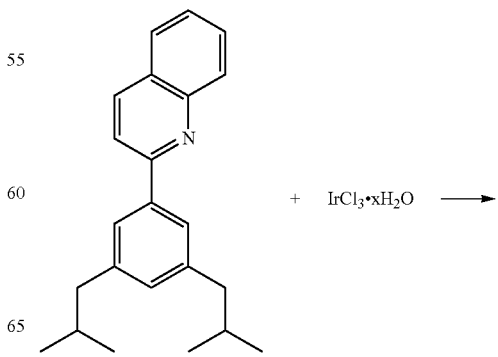

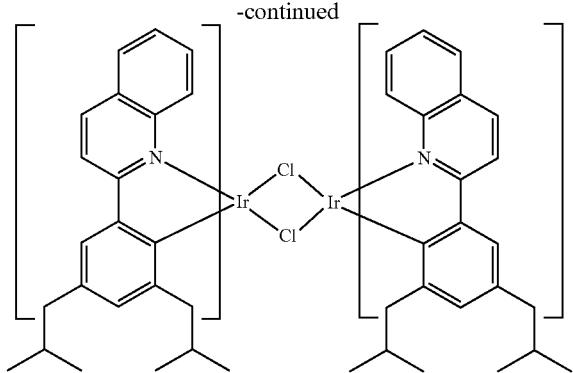

Ligand from step 3 (20 g, 65 mmol), iridium chloride (5.0 g, 14 mmol), 2-ethoxyethanol (75 mL) and water (12.5 mL) was charged in a 250 mL round bottom flask. The reactor contents were heated to 102° C. under an atmosphere of nitrogen for 16-19 h. The dichloro iridium bridged dimer was not isolated.

Step 5

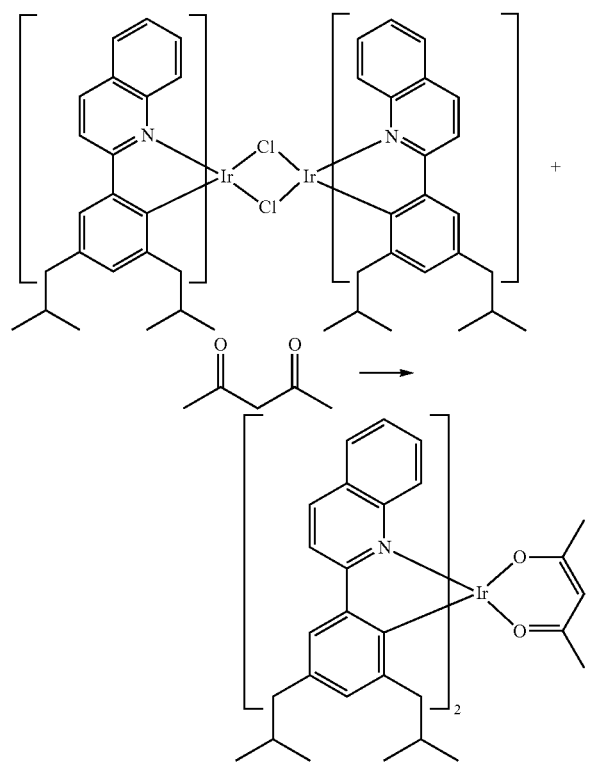

The reactor contents from step 4 were cooled to anmbient. 2,4-pentanedione (14.0 g 140 mmol) and sodium carbonate (30.0 g, 280 mmol) were added to the reactor. The reaction mixture was stirred at ambient for 24 h. 5 g of celite and 500 mL of dichloromethane was added to the reaction mixture to dissolve the product. The mixture was then filtered through a bed of celite. The filtrate was then passed through a through a silica/alumina plug and washed with dichloromethane. The clarified solution was then filtered through GF/F filter paper the filtrate was heated to remove most of the dichloromethane. 20 mL of isopropanol was then added and the slurry was cooled to ambient and the product was filtered and washed with isopropanol and dried to give 7.1 g of crude product (55% yield). This product was then recrystallised twice using dichloromethane and isopropanol and then sublimed.

Synthesis of Compound 5

Step 1

2-chloroquinoline (9.0 g, 54.4 mmol), 3,5-dimethylphenylboronic acid (9.2 g, 59.8 mmol), Pd(PPh3)$_4$ (1.8 g, 1.5 mmol), $K_2CO_3$ (22.4 g, 163 mmol), 1,2-dimethoxyethane (150 mL) and water (150 mL) were charged in a 500 mL round bottom flask. The reaction mixture was heated to reflux under nitrogen for 18 h. The reaction mixture was then cooled to ambient and the organic phase was separated from the aqueous phase. The aqueous phase was washed with ethyl acetate and all the organic components were combined and dried over anhydrous magnesium sulphate. The solvent was then removed under vacuum and the product was purified using silica gel chromatography (10% ethyl acetate in hexane as eluent). The material obtained was further purified by vacuum distillation to yield 12.2 g (95% yield) of product as a colorless oil.

Step 2

The ligand from step 1 (46 g, 197.4 mmol), 2-ethoxyethanol (536 mL) and water (178 mL) were charged in a 1 L three-neck round bottom flask. Nitrogen gas was bubbled through the reaction mixture 45 min. IrCl₃.H₂O (32.0 g 86.2 mmol) was then added and the reaction mixture was heated to reflux under nitrogen for 17 hours. The reaction mixture was cooled to ambient and filtered. The dark gray residue was washed with methanol (4×150 mL) followed by hexanes (3×300 mL). 36.5 gram of the dichlorobridged Iridium dimer was obtained after drying in vacuum oven.

Step 3

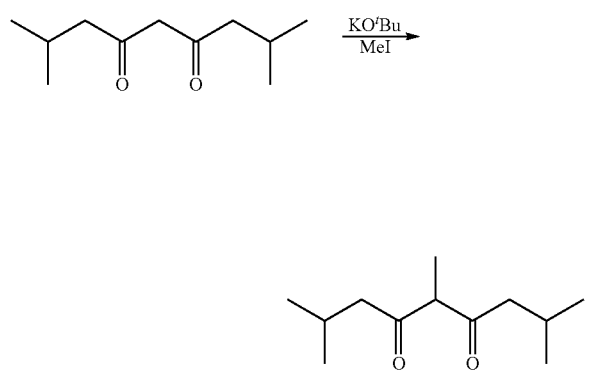

2,8-dimethylnonane-4,6-dione (10.0 g, 5.4 mmol), potassium tert butoxide (7.0 g, 6.5 mmol) and 150 mL of anhydrous THF was charged in a 3neck 250 mL dry round bottom flask. The reaction mixture was stirred under an atmosphere of nitrogen at ambient for 1 h. Iodomethane (15 g, 105 mmol) was added to the reaction mixture via a needle and syringe. The reaction mixture was continued to stir at ambient for a further 4 h. The reaction was monitored by GC. The reaction was quenched with 100 mL of water and acidified using 1M hydrochloric acid. The product was extracted with ethyl acetate and chromatographed using silica gel chromatography (using 1-5% ethyl acetate in hexanes). HPLC revealed that the product (2,5,8-trimethyl-nonane-4,6-dione) contained a mixture of 2,8-dimethyl-nonane-4,6-dione (starting material). These to products were separated via chromatography using deactivated basic alumina with 1-5% ethyl acetate in hexanes as the mobile phase to give 3.6 g of product (33% yield).

Step 4

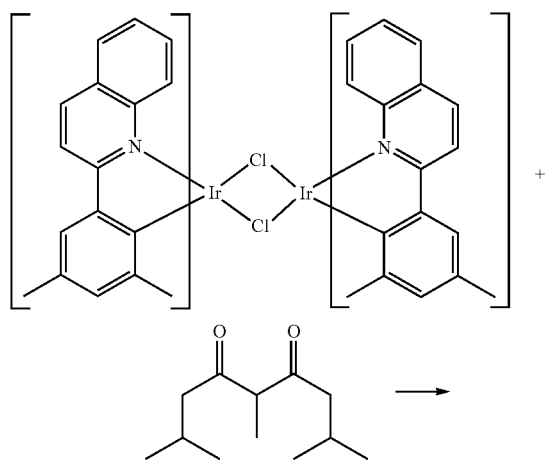

-continued

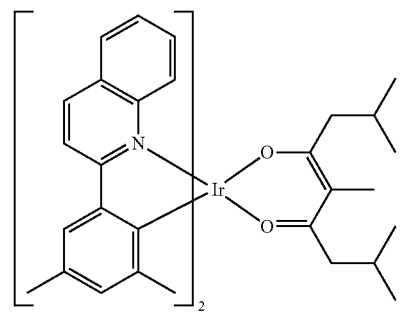

Dichlorobridged Iridium dimer from step 2 (1.0 g, 0.7 mmol), 10 mol eq 2,5,8-trimethylnonane-4,6-dione (1.4 g,), 20 mol eq of Na₂CO₃ (2.0 g) and 25 mL of 2-ethoxyethanol were placed in a 250 mL round bottom flask. The reaction mixture was stirred at ambient for 24 hours. 1 g of celite and 100 mL of dichloromethane was added to the reaction mixture to dissolve the product. The mixture was then filtered through a bed of celite. The filtrate was then passed through a through a silica/alumina plug and washed with dichloromethane. The clarified solution was then filtered through GF/F filter paper the filtrate was heated to remove most of the dichloromethane. 10 mL of isopropanol was then added and the slurry was cooled to ambient and the product was filtered and washed with isopropanol and dried to give 0.7 g of crude product (57% yield). This product was then recrystallised twice using dichloromethane and isopropanol and then sublimed.

Synthesis of Compound 6

Step 1

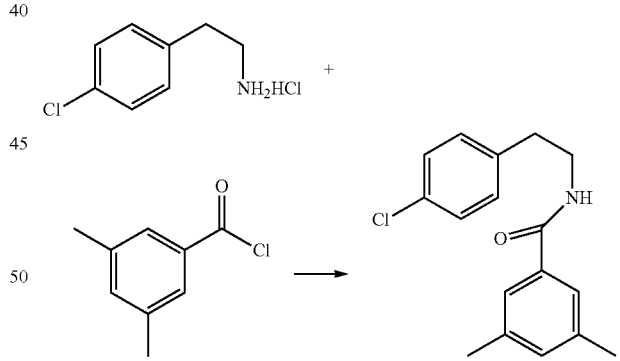

4-chlorophenylethylamine hydrochloride (10.0 g, 64 mmol), pyridine (15.3 g, 193 mmol) and dichloromethane (50 mL) were added to a 3-neck round bottom flask. The solution was cooled in an ice bath and 3,5-dimethylbenzoyl chloride (10.8 g, 64 mmol) was added slowly. The solution was allowed to warm to room temperature and stirred for 12 hours. Dichloromethane was added and the organic phase was washed with water, followed by 5% HCl solution, then 5% NaOH solution and then dried over anhydrous MgSO₄. The solvent was evaporated under vacuum resulting in 15 g of crude product (82% yield) which was used without further purification.

Step 2

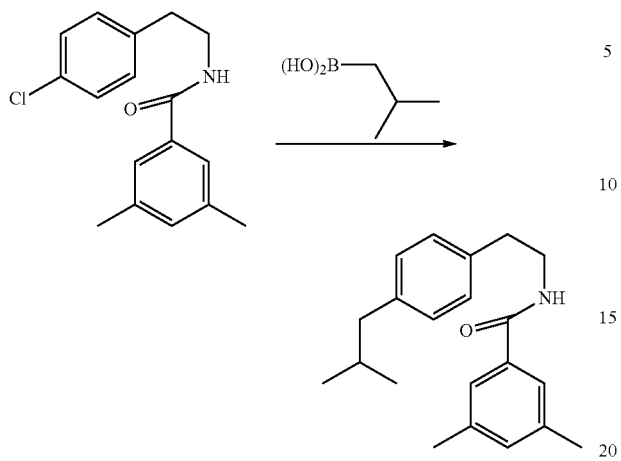

N-(4-chlorophenylethyl)benzamide (15 g, 52 mmol), isobutylboronic acid (10.6 g, 104 mmol), Pd₂(dba)₃ (1 mol %), 2-dicyclohexylphosphino-2',6'-dimethoxybiphenyl (4 mol %), potassium phosphate monohydrate (22.0 g 212 mmol) 200 ml of toluene was charged in a 250 mL round bottom flask. Nitrogen was bubbled through the reaction mixture for 20 minutes and heated to reflux for 18 h overnight. The reaction mixture was allowed to cool to ambient temperature and the crude product was purified by column chromatography using 2% ethyl acetate in hexanes as solvent. 15 g of desired product was obtained (93% yield).

Step 3

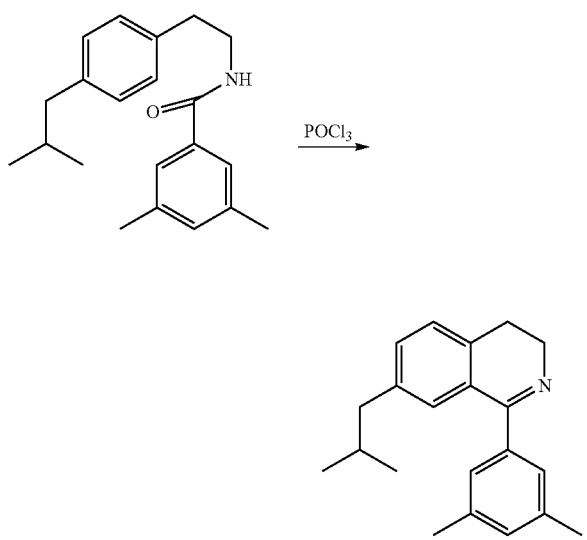

N-(4-p-isobutylphenylethyl)benzamide (15.0 g), phosphorous pentoxide (50 g) phosphorous oxychloride 50 mL and xylenes (160 mL) was refluxed for 3 h in a 1 L round bottom flask. After the reaction mixture was allowed to cool to room temperature, the solvent was decanted and ice was slowly added to the solid in the bottom of the flask. The water-residue mixture was made weakly alkaline with 50% NaOH and the product was extracted with toluene. The organic layer was washed with water and dried over anhydrous MgSO₄. The solvent was evaporated to give 12.4 g of crude product (88% yield) which was used without further purification.

Step 4

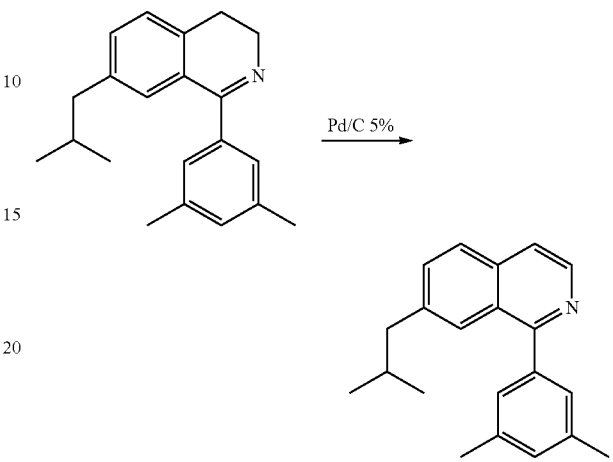

1-(3,5-dimethylphenyl)-7-isobutyl-3,4-dihydroisoquinoline (12.4 g, 42.5 mmol) and 2 g of 5% Pd/C (~10% by weight) were added to a 500 mL round bottom flask with 100 mL of xylenes. The solution was refluxed for 24 hrs and the formation of the product was monitored by TLC. The solvent was removed under vacuum and the product was purified by silica gel column chromatography with 5% ethyl acetate in hexanes as the eluent. The product was then vacuum distilled to give (6.0 g, 21 mmol) of pure product.

Step 5

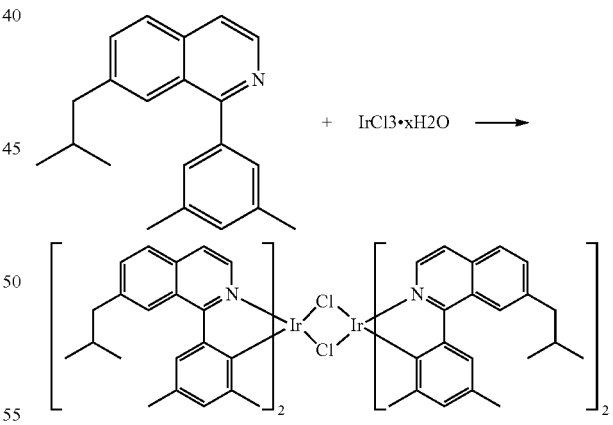

The ligand from step 4 (4.7 g, 14 mmol), 2-ethoxyethanol (25 mL) and water (5 mL) were charged in a 1 L three-neck round bottom flask. Nitrogen gas was bubbled through the reaction mixture for 45 min. IrCl₃.H₂O (1.2 g 3.6 mmol) was then added and the reaction mixture was heated to reflux under nitrogen for 17 hours. The reaction mixture was cooled to ambient and filtered. The dark red residue was washed with methanol (2×25 mL) followed by hexanes (2×25 mL). 2.5 g of the dichlorobridged Iridium dimer was obtained after drying in vacuum oven.

Step 6

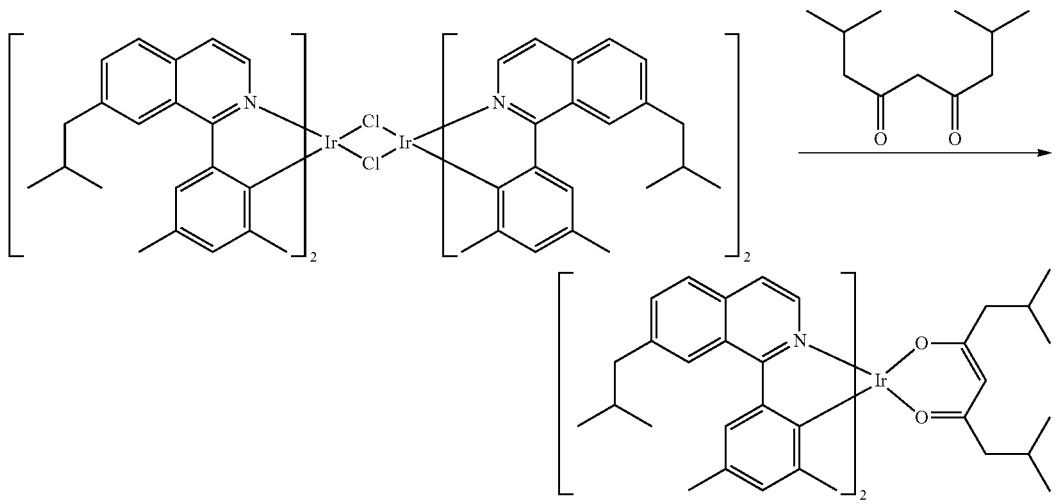

Dichlorobridged Iridium dimer from step 5 (2.5 g, 1.5 mmol), 10 mol eq 2,8-dimethylnonane-4,6-dione (2.8 g,), 20 mol eq of $Na_2CO_3$ (4.3 g) and 25 mL of 2-ethoxyethanol were placed in a 250 mL round bottom flask. The reaction mixture was stirred at ambient for 24 hours. 2 g of celite and 200 mL of dichloromethane was added to the reaction mixture to dissolve the product. The mixture was then filtered through a bed of celite. The filtrate was then passed through a through a silica/alumina plug and washed with dichloromethane. The clarified solution was then filtered through GF/F filter paper the filtrate was heated to remove most of the dichloromethane. 20 mL of isopropanol was then added and the slurry was cooled to ambient and the product was filtered and washed with isopropanol and dried to give 2.5 g of crude product (86% yield). This product was then recrystallised twice using dichloromethane and isopropanol and then sublimed.

Synthesis of Compound 7

Step 1

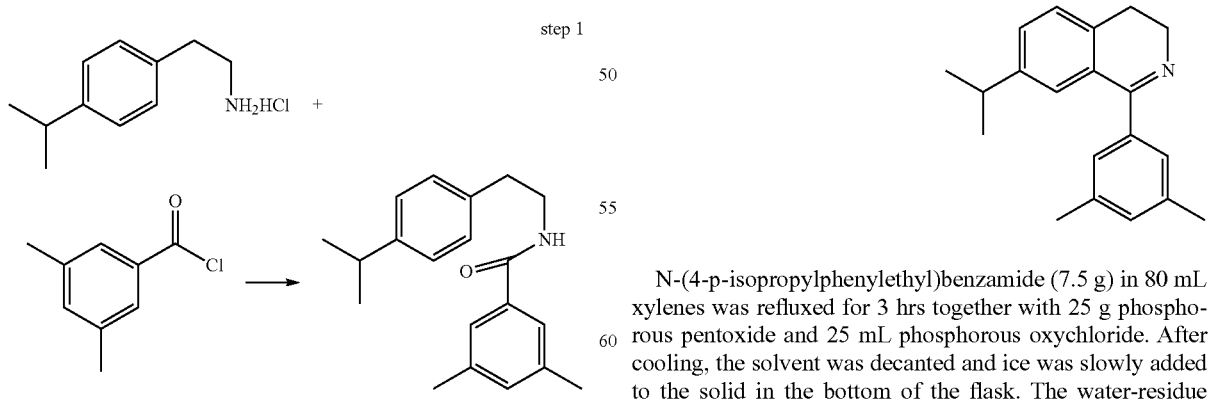

4-isopropylphenylethylamine hydrochloride (5.0 g, 25 mmol), pyridine (5.9 g, 75 mmol) and dichloromethane (25 mL) were added to a 3-neck round bottom flask. The solution was cooled in an ice bath and 3,5-dimethylbenzoyl chloride (4.2 g, 25 mmol) was added slowly. The solution was then allowed to warm to room temperature and stirred for 12 hours. Dichloromethane was added and the organic phase was washed with water, followed by 5% HCl solution, then 5% NaOH solution and then dried over anhydrous $MgSO_4$. The solvent was evaporated under vacuum resulting in 7.5 g of crude product (82% yield) which was used without further purification.

Step 2

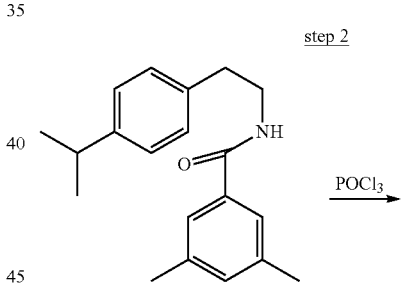

N-(4-p-isopropylphenylethyl)benzamide (7.5 g) in 80 mL xylenes was refluxed for 3 hrs together with 25 g phosphorous pentoxide and 25 mL phosphorous oxychloride. After cooling, the solvent was decanted and ice was slowly added to the solid in the bottom of the flask. The water-residue mixture was made weakly alkaline with 50% NaOH and the product was extracted with toluene. The organic layer was washed with water and dried over anhydrous $MgSO_4$. The solvent was removed under vacuum to give 6.2 g of crude product which was used without further purification.

Step 3

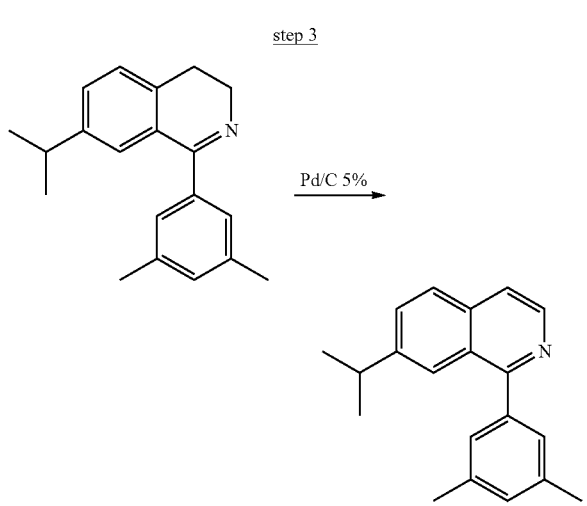

6.2 g of 7-isopropyl-1-phenyl-3,4-dihydroisoquinoline and 1 g of 5% Pd/C (~10% by weight) were added to a round bottom flask with 100 mL of xylenes. The solution was refluxed for 24 hrs and the formation of the product was monitored by TLC. The xylenes solvent was removed and the product was purified by column chromatography with ethyl acetate/hexanes. The pure fractions were collected and the solvent was removed. The product was then distilled in a kugelrohr apparatus at 185° C. affording 1.8 g (0.0073 mol) of pure product. The overall yield of ligand formation was ~15%.

Step 4

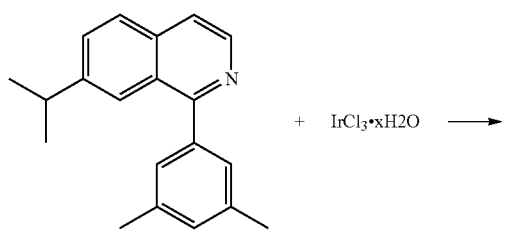

The ligand from step 3 (1.8 g, 7.3 mmol), 2-ethoxyethanol (25 mL) and water (5 mL) were charged in a 1 L three-neck round bottom flask. Nitrogen gas was bubbled through the reaction mixture 45 min. IrCl$_3$.H$_2$O (1.2 g 3.6 mmol) was then added and the reaction mixture was heated to reflux under nitrogen for 17 hours. The reaction mixture was cooled to ambient and filtered. The dark red residue was washed with methanol (2×25 mL) followed by hexanes (2×25 mL). 1.3 gram of the dichlorobridged Iridium dimer was obtained after drying in vacuum oven Step 5

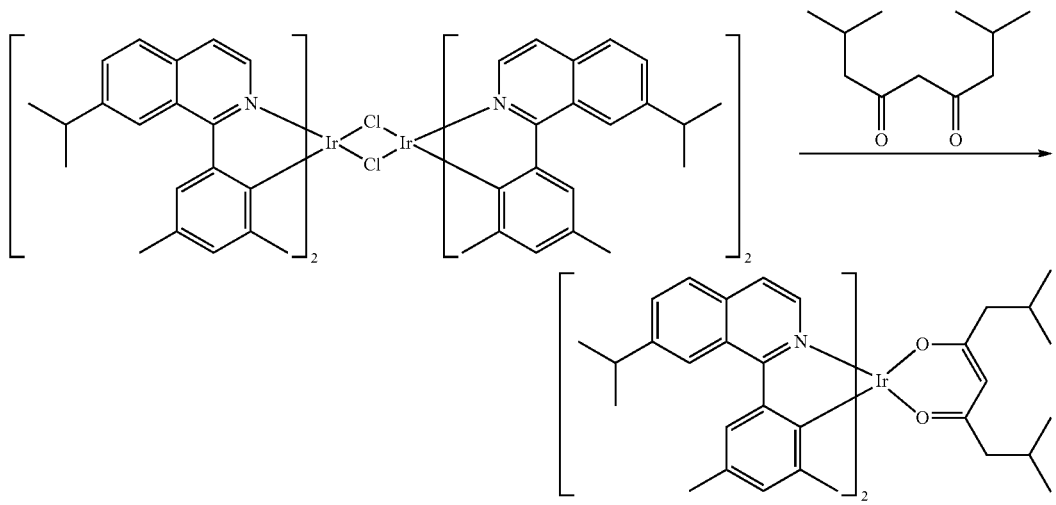

Dichlorobridged Iridium dimer from step 2 (1.3 g, 0.9 mmol), 10 mol eq 2,8-dimethylnonane-4,6-dione (1.6 g,), 20 mol eq of Na$_2$CO$_3$ (2.5 g) and 25 mL of 2-ethoxyethanol were placed in a 250 mL round bottom flask. The reaction mixture was stirred at ambient for 24 hours. 2 g of celite and 200 mL of dichloromethane was added to the reaction mixture to dissolve the product. The mixture was then filtered through a bed of celite. The filtrate was then passed through a through a silica/alumina plug and washed with dichloromethane. The clarified solution was then filtered through GF/F filter paper the filtrate was heated to remove most of the dichloromethane. 20 mL of isopropanol was then added and the slurry was cooled to ambient and the product was filtered and washed with isopropanol and dried to give 1.4 g of crude product (92% yield). This product was then recrystallised twice using dichloromethane and isopropanol and then sublimed.

Synthesis of Compound 8

Step 1

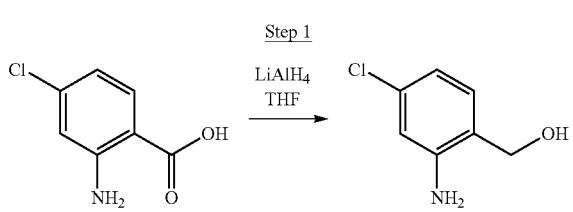 [SMILES: Nc1cc(Cl)ccc1C(=O)O ; Nc1cc(Cl)ccc1CO]

2-amino-4-clorobenzoic acid (42.8 g, 0.25 mol) was dissolved in 200 mL of anhydrous THF and cooled in an ice-water bath. To the solution was added lithium aluminum hydride chips (11.76 g, 0.31 mol). The resulting mixture was stirred at room temperature for 8 hours. 12 g of water was added, and then 12 g 15% NaOH. 36 g of water was then added. The slurry was stirred at room temperature for 30 min. The slurry was filtered. The solid was washed with ethyl acetate. The liquid was combined and the solvent was evaporated. The crude material was used for next step without purification.

Step 2

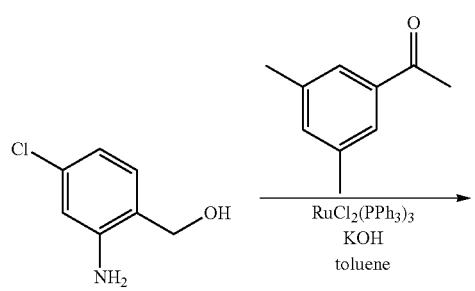

2-amino-4-chlorophenyl)methanol (6.6 g, 0.04 mol) 1-(3,5-dimethylphenyl)ethanone(10.0 g 0.068 mol), RuCl2(PPh3)3 0.1 g) and 2.4 g of KOH was refluxed in 100 ml of toluene for 10 hours. Water was collected from the reaction using a Dean-Stark trap. After the reaction was cooled to room temperature, the mixture was filtered through a silica gel plug. The product was further purified with column chromatography using 2% ethyl acetate in hexanes as eluent. 9 g product was obtained after column. The product was further recrystallized from isopropanol. 5 g of desired product was obtained.

Step 3

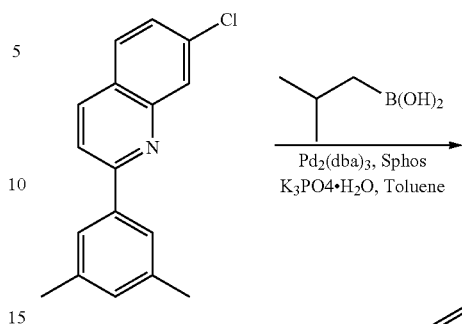

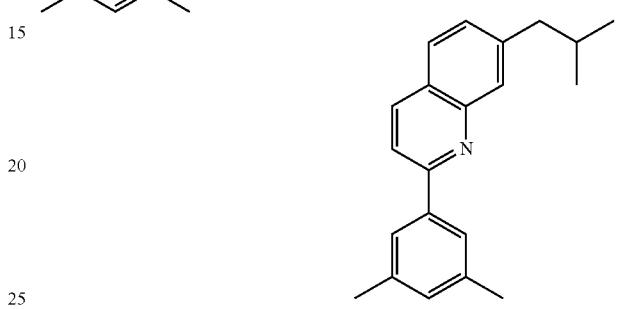

7-chloro-2-(3,5-dimethylphenyl)quinoline (3.75 g, 0.014 mol) isobutylboronic acid (2.8 g, 0.028 mol), Pd$_2$(dba)$_3$ (1 mol %), 2-dicyclohexylphosphino-2',6'-dimethoxybiphenyl (4 mol %), potassium phosphate monohydrate(16.0 g) 100 mL of toluene was charged in a 250 mL round bottom flask. Nitrogen was bubbled through the reaction mixture for 20 minutes and heated to reflux for 18 h overnight. The reaction mixture was allowed to cool to ambient temperature and the crude product was purified by column chromatography using 2% ethyl acetate in hexanes as solvent. 3.6 g of desired product was obtained.

Step 4

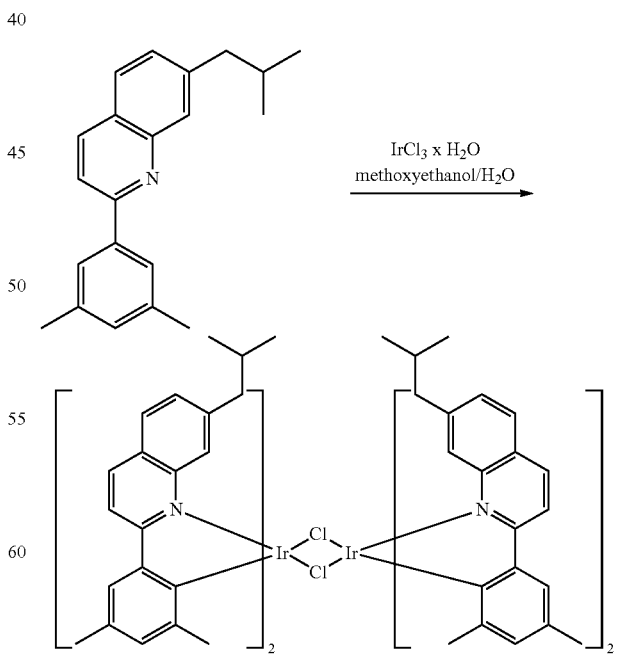

The ligand from step 3 (4.6 g, 16 mmol), 2-ethoxyethanol (25 mL) and water (5 mL) were charged in a 1 L three-neck round bottom flask. Nitrogen gas was bubbled through the reaction mixture 45 min. IrCl$_3$.H$_2$O (1.2 g 3.6 mmol) was then added and the reaction mixture was heated to reflux under nitrogen for 17 hours. The reaction mixture was cooled to ambient and filtered. The dark red residue was washed with methanol (2×25 mL) followed by hexanes (2×25 mL). 1.3 gram of the dichlorobridged Iridium dimer was obtained after drying in vacuum oven Step 5

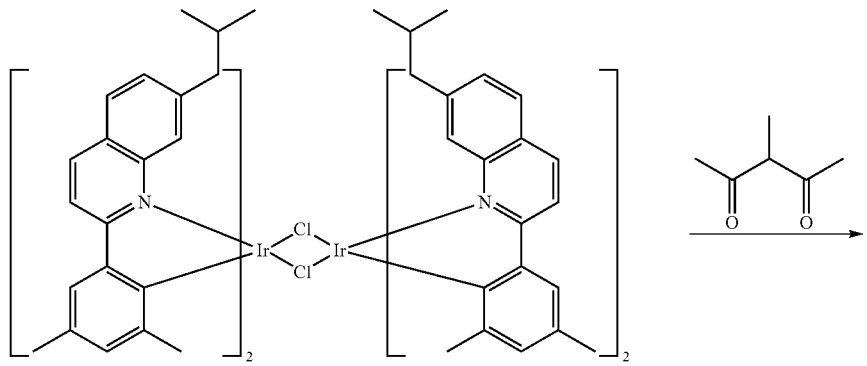

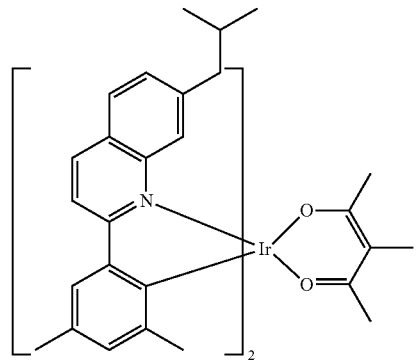

Dichlorobridged Iridium dimer from step 2 (1.0 g, 0.6 mmol), 10 mol eq 3-methyl-2,4-pentanedione (0.8 g,), 20 mol eq of Na$_2$CO$_3$ (3 g) and 25 mL of 2-ethoxyethanol were placed in a 250 mL round bottom flask. The reaction mixture was stirred at ambient for 24 hours. 2 g of celite and 200 mL of dichloromethane was added to the reaction mixture to dissolve the product. The mixture was then filtered through a bed of celite. The filtrate was then passed through a through a silica/alumina plug and washed with dichloromethane. The clarified solution was then filtered through GF/F filter paper the filtrate was heated to remove most of the dichloromethane. 20 mL of isopropanol was then added and the slurry was cooled to ambient and the product was filtered and washed with isopropanol and dried to give 1.1 g of crude product (97% yield). This product was then recrystallised twice using dichloromethane and isopropanol and then sublimed.

Synthesis of Compound 9

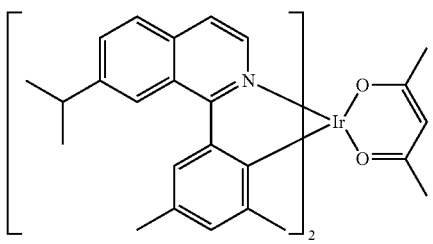

Compound 9 can be synthesized using the same procedure as outlined for invention compound 7. In this case the dichlorobridged iridium dimer that is formed should be cleaved with 2,4-pentane dione to afford the product.

Synthesis of Compound 10

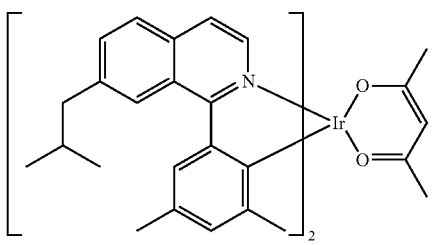

Compound 10 can be synthesized using the same procedure as outlined for invention compound 6. In this case the dichlorobridged iridium dimer that is formed should be cleaved with 2,4-pentane dione to afford the product.

Synthesis of Compound 11

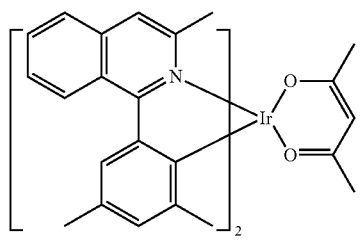

Synthesis of compound 11 can be easily synthesized using common synthetic approaches already disclosed.

Synthesis of Compound 12

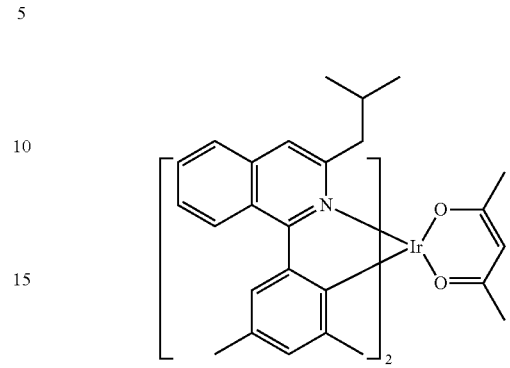

Synthesis of compound 11 can be easily synthesized using common synthetic approaches already disclosed.

Device Examples

All device examples were fabricated by high vacuum ($<10^{-7}$ Torr) thermal evaporation. The anode electrode is 1200 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

The organic stack of the Device Examples 1-7 in Table 2, consisted of sequentially, from the ITO surface, 100 Å of Ir(3-Meppy)3 as the hole injection layer (HIL), 400 Å of 4,4'-bis[N-(1-naphthyl)-N-phenylamino]biphenyl (α-NPD) as the hole transporting later (HTL), 300 Å of BAlq doped with 8-12% of the inventive compound as the emissive layer (EML), and 550 Å of $Alq_3$ (tris-8-hydroxyquinoline aluminum) as the ETL.

Comparative Examples 1 and 2 were fabricated similarly to the Device Examples, except that Ir(3-Mepq)$_2$(acac) or Ir(piq)$_2$(acac) was used as the emissive dopant.

The device structures and data are summarized in Table 2. As used herein, the following compounds have the following structures:

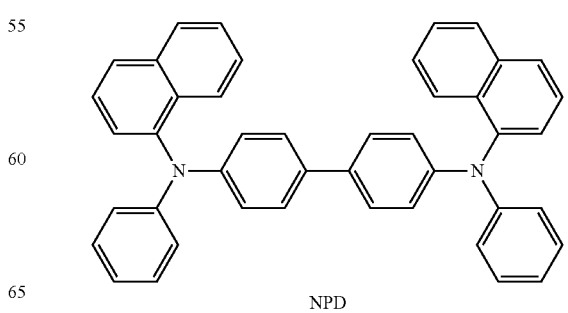

NPD

-continued

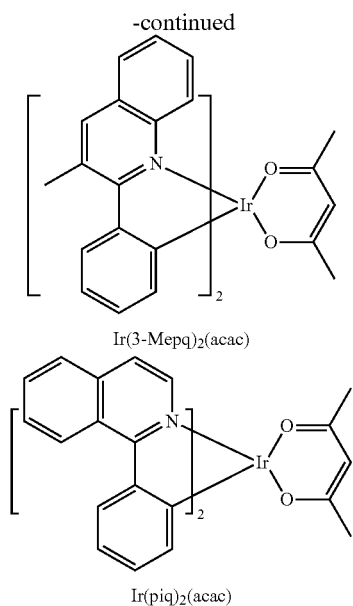

Ir(3-Mepq)₂(acac)

Ir(piq)₂(acac)

which has LE and EQE of 14.3cd/A and 14.1% and has slightly bluer CIE (0.65, 0.35). Additionally, the LE and EQE of Example 6 are 14.0cd/A and 20.4% respectively, at CIE of (0.691, 0.307) and the LE and EQE of Example 7 are 13.3cd/A and 19.4% respectively, at CIE of (0.690, 0.307), compared to Comparative Example 2 which has LE and EQE of 11.1cd/A and 15.4% at CIE (0.68, 0.32). Of note is that even though these examples are much deeper red than our Comparative Example 2, the efficiencies for these examples are still significantly higher. The Full Width Half Max (FWHM) of the EL for examples 3, 4, 6 and 7 are 59, 61, 55and 55 nm respectively. These are by far narrower than the EL measured for Comparative Examples 1 and 2 with FWHM 94 and 84 nm, respectively. Device Examples 6 and 7have the narrowest FWHM of any red iridium complex reported to date. Therefore, the inventive compounds may be advantageously used in devices to improve efficiency, stability and luminescence. The sublimation temperatures using the branched diketone ligand, for example, Compounds 3, 6 and 7, are also quite low which are well suited for long term thermal evaporation required in manufacturing.

Additionally, the 70° C. lifetime comparison shows that Device Example 7is more stable than both Comparative Example 1 and 2. Therefore, the inventive compounds may be advantageously used in devices to improve device lifetime.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as

TABLE 2

| Device Example | Emitter (doping %) | $T_{sub}$ at 0.24 Å/s | At 10 mA/cm² | | | | | | | At 40 mA/cm² | |
| --- | --- | --- | --- | --- | --- | --- | --- | --- | --- | --- | --- |
| | | | $Em_{max}$ (nm) | FWHM (mn) | CIE | V (V) | LE (cd/A) | EQE (%) | LE:EQE | $L_0$ (cd/m²) | $T_{0.8}$ at 70° C. |
| comparative 1 | Ir(3-Mepq)₂(acac) (9) | 206 | 622 | 94 | 0.65 0.35 | 8.1 | 14.3 | 14.1 | 1.01 | 4,817 | 60 |
| comparative 2 | Ir(piq)₂(acac) (9) | 229 | 632 | 84 | 0.68 0.32 | 8.8 | 10.6 | 15.2 | 0.70 | 3,757 | 240 |
| 1 | 1 (8) | 177 | 634 | 68 | 0.682 0.316 | 8.6 | 12.6 | 16.2 | 0.78 | 4,200 | 70 |
| 2 | 2 (8) | 198 | 636 | 66 | 0.688 0.308 | 8.5 | 8.5 | 13 | 0.66 | 2,895 | 80 |
| 3 | 3 (8) | 180 | 618 | 59 | 0.662 0.335 | 8.4 | 21.1 | 18.2 | 1.16 | 7,042 | 55 |
| 4 | 4 (12) | 186 | 621 | 61 | 0.666 0.331 | 9.2 | 18.7 | 17.4 | 1.07 | 6,443 | 31 |
| 5 | 5 (12) | 190 | 633 | 67 | 0.681 0.316 | 8.5 | 11.9 | 15.3 | 0.78 | 4,029 | 25 |
| 6 | 6 (12) | 205 | 631 | 55 | 0.691 0.307 | 8.5 | 14.0 | 20.4 | 0.68 | 4,694 | 69 |
| 7 | 7 (12) | 210 | 632 | 55 | 0.690 0.307 | 8.1 | 13.3 | 19.4 | 0.68 | 4,493 | 190 |

It can be seen from Table 2 that the Device Examples containing inventive compounds show similar or higher device efficiency and lifetime and also extremely narrow emission spectra versus the Comparative Examples containing Ir(3-Mepq)₂(acac) or Ir(piq)₂(acac). Several of the Device Examples show particularly good properties. For example, the LE and EQE of Example 3 are 21.1 cd/A and 18.2% respectively, at CIE of (0.662, 0.335). Also, the LE and EQE of Example 4 are 18.7 cd/A and 11.4% respectively, at CIE of (0.666, 0.331). These efficiencies are significantly higher than that for Comparative Example 1,

What is claimed is:

1. A compound selected from the group consisting of:

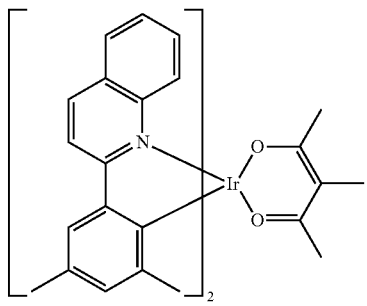

Compound 1

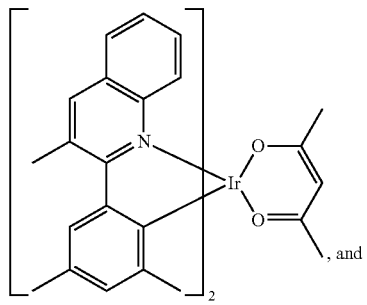

Compound 2

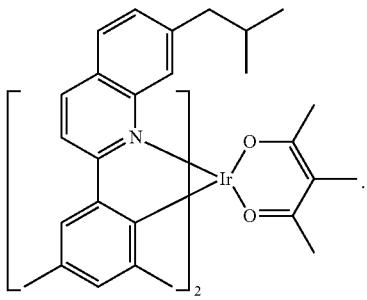

Compound 8

2. The compound of claim 1, wherein the compound is:

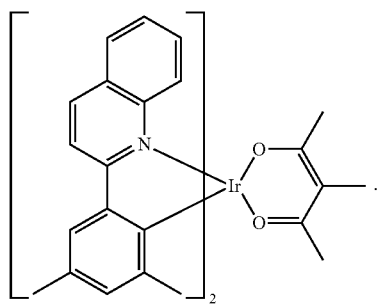

Compound 1

3. The compound of claim 1, wherein the compound is:

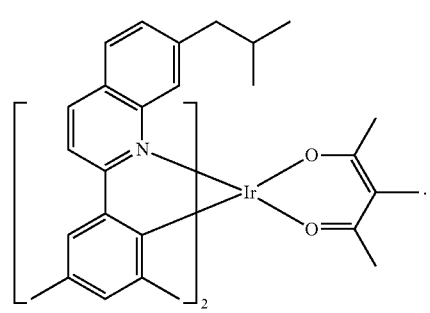

Compound 8

4. The compound of claim 1, wherein the compound is:

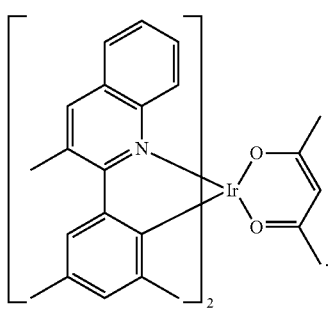

Compound 2

5. An organic light emitting device comprising:
   an anode;
   a cathode; and
   an organic layer, disposed between the anode and the cathode, the organic layer comprising a compound selected from the group consisting of:

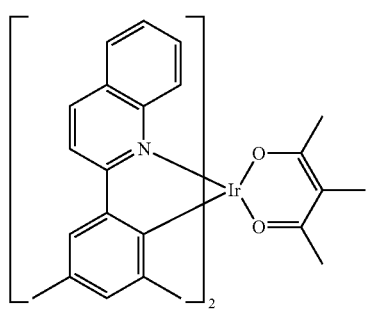

Compound 1

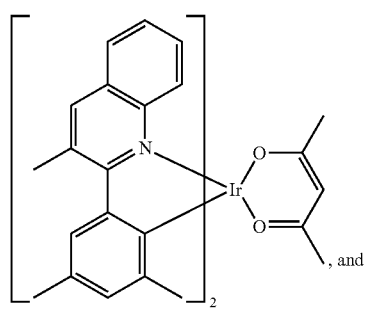

Compound 2

-continued

Compound 8

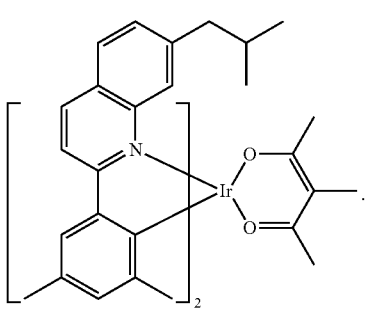

6. The device of claim 5, wherein the compound is:

Compound 1

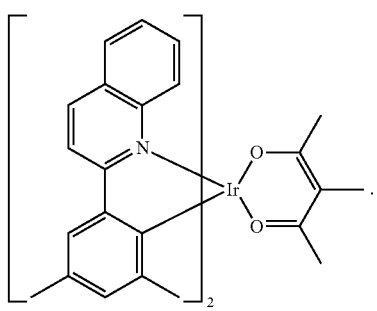

7. The device of claim 5, wherein the compound is:

Compound 8

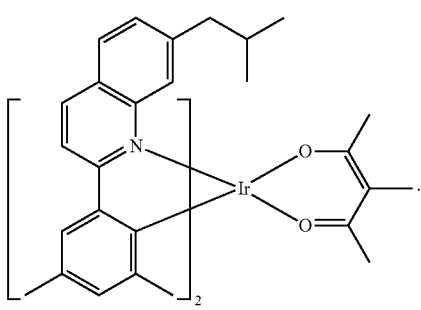

8. The device of claim 5, wherein the compound is:

Compound 2

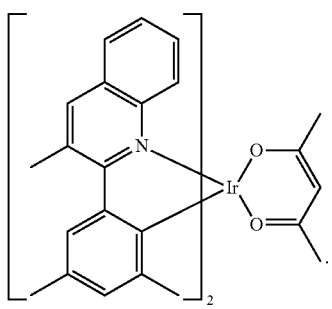

9. The device of claim 5, wherein the organic layer is an emissive layer comprising the compound and a host.

10. The device of claim 9, wherein the compound is an emissive material.

11. The device of claim 9, wherein the host is a metal coordination complex.

12. The device of claim 11, wherein the host is BAlq.

13. The device of claim 9, wherein the compound is an emissive material and the host is a metal coordination complex.

14. The device of claim 13, wherein the host is BAlq.

* * * * *